US010045978B2

(12) United States Patent
Moussy et al.

(10) Patent No.: US 10,045,978 B2
(45) Date of Patent: Aug. 14, 2018

(54) TREATMENT OF MASTOCYTOSIS WITH MASITINIB

(71) Applicant: AB SCIENCE, Paris (FR)

(72) Inventors: Alain Moussy, Paris (FR); Jean-Pierre Kinet, Aix en Provence (FR)

(73) Assignee: AB SCIENCE, Paris (FR)

( * ) Notice: Subject to any disclaimer, the term of this patent is extended or adjusted under 35 U.S.C. 154(b) by 0 days.

(21) Appl. No.: 14/957,201

(22) Filed: Dec. 2, 2015

(65) Prior Publication Data

US 2016/0089368 A1 Mar. 31, 2016

Related U.S. Application Data

(63) Continuation-in-part of application No. 14/875,152, filed on Oct. 5, 2015, which is a continuation-in-part of application No. 13/881,043, filed as application No. PCT/EP2011/069285 on Nov. 3, 2011, now abandoned.

(60) Provisional application No. 61/410,594, filed on Nov. 5, 2010.

(51) Int. Cl.
| | |
|---|---|
| *A61K 31/496* | (2006.01) |
| *A61K 9/00* | (2006.01) |
| *A61K 31/095* | (2006.01) |

(52) U.S. Cl.
CPC .......... *A61K 31/496* (2013.01); *A61K 9/0053* (2013.01); *A61K 31/095* (2013.01)

(58) Field of Classification Search
CPC ............................ A61K 31/496; A61K 9/0053
USPC .................................................. 514/252.12
See application file for complete search history.

(56) References Cited

U.S. PATENT DOCUMENTS

| | | | |
|---|---|---|---|
| 2004/0110810 A1* | 6/2004 | Ciufolini .............. | C07D 277/42 514/370 |
| 2005/0054617 A1 | 3/2005 | Moussy et al. | |

FOREIGN PATENT DOCUMENTS

| | | |
|---|---|---|
| EP | 1525200 | 10/2007 |
| WO | 2004/014903 | 2/2004 |
| WO | 2008/098949 | 8/2008 |

OTHER PUBLICATIONS

Droogendijk et al. Cancer (2006) vol. 107, pp. 345-351.*
Hermine et al. PLoS ONE (2008), vol. 3, e2266.*
ClinicalTrials.gov [online]. NCT00831974 Retrieved on: Dec. 8, 2016 Retrievd from the internet <url:https://web.archive.org/web/20090904032036/http://clinicaltrials.gov/ct2/show/NCT00831974>.*
Akin. Journal Molecular Diagnostics (2006), vol. 8, pp. 412-419.*
Paul et al.; "Masitinib for the treatment of systemic and cutaneous mastocystosis with handicap: A phase 2a study" Am J. Hematol. (2010), vol. 85, pp. 921-925.
Dubreuil et al.; "Masitinib (AB1010), a Potent . . . Targeting Kit". Plos one, Public Library of Science, vol. 4, No. 9, Sep. 1, 2009, pp. 1-12.
Moura et al.; "Depression in . . . Masitinib Therapy", Plos One, vol. 6, No. 10, Jan. 1, 2011, p. E26375.
Gilfillan et al.; "Integrated Signaling . . . mast-cell activation", Nature Publishing Group, vol. 6, Mar. 2006, pp. 218-230.
Hamilton, "A Rating Scale for Depression", J. Nerol. Neurosurg, Psychiat., 1960, 23, pp. 56-62.
Hermine et al.; "Case-Control Cohort . . . Disability in Mastocytosis", Plos One, vol. 3, Issue 5, May 5, 2008, E2266.
Humbert et al.; "Masitinib Combined . . . Mouse Model", Plos One, vol. 5, Issue 3; Mar. 3, 2010, E9430.
Lim, et al.; "Cytoreductive therapy . . . mesylate or 2-chlorodeoxyadenosine", American Journal of Hematology, 2009, pp. 790-794.
Mitry et al.; "Safety and Activity . . . Pancreatic Cancer", Cancer Chemother. Pharmacol., Feb. 2010.
Reber et al.; "Stem Cell . . . Inflammatory diseases", European Journal of Pharmacology, 533 (2006) pp. 327-340.
Droogendijk et al.; Imatinib Mesylate in the treatment of Systemic Mastocytosis. Cancer (2006) vol. 107, pp. 345-351.
Hermine et al.; "Case-Control Cohort Study of Patients' Perceptions of Disability in Mastocytosis", PLoS ONE (2008), vol. 3, E2266.
Humbert et al.; "Masitinib, a c-kit/PDGF receptor tyrosine kinase inhibitor, improves disease control in severe corticosteriod-dependent asthmatics", Allergry (2009) vol. 64, pp. 1194-1201.
Gleixner et al.; "Synergistic growth-inhibitory effects of two tyrosine kinase inhibitors, dasatinib and PKC412, on neoplastic mast cells expressing the D916V-mutated oncogenic variant of KIT", Haematologica (2007), vol. 92, pp. 1451-1459.
Valent, "Diagnosis and Treatment . . . State of the Art", British Journal of Haematology, 2003, 122, pp. 695-717.
Vega-Ruiz et al., "Phase II study . . . systemic mastocytosis", Leukemia Research, (2009).
Verstovsek et al., "Phase II Study . . . Systemic Mastocytosis", Clinical Cancer Research, 14(12), Jun. 15, 2008, pp. 3906-3915.
Arock et al., "Current treatment options in patients with mastocytosis: status in 2015 and future perspectives", European Journal of Haematology, Jun. 2015; 94(6):474-490.
Clinical Trial AB06006—Sep. 2012, available at https://clinicaltrials.gov/ct2/show/NCT00814073.
Fisk et al., "Measuring the Functional Impact of Fatigue: Initial Validation of the Fatigue Impact Scale", Clinical Infectious Diseases, Jan. 1994; vol. 18, Supplement 1:S79-S83.
Molderings et al., "Mast cell activation disease: a concise practical guide for diagnostic workup and therapeutic options", Journal of Hematology & Oncology, Mar. 22, 2011;4:10.
Valent et al., "Definitions, Criteria and Global Classification of Mast Cell Disorders with Special Reference to Mast Cell Activation Syndromes: A Consensus Proposal", International Archives of Allergy and Immunology, 2012, 157:215-225.
Akin et al., "Mast cell activation syndrome: Proposed diagnostic criteria", J. Allergy Clin. Immunol., 2010, 126(6):1099-1104.

(Continued)

Primary Examiner — Melenie Lee McCormick
Assistant Examiner — Taina D Matos Negron
(74) Attorney, Agent, or Firm — Younng & Thompson

(57) ABSTRACT

The treatment of mastocytosis, and in particular indolent forms of mastocytosis (including smoldering systemic, indolent systemic and cutaneous mastocytosis), including the administration of a tyrosine kinase inhibitor or a mast cell inhibitor, especially masitinib or a pharmaceutically acceptable salt or solvate thereof, in particular in an appropriate dosage regimen.

18 Claims, No Drawings

(56) References Cited

OTHER PUBLICATIONS

Gilfillan et al., "The tyrosine kinase network regulating mast cell activation", Immunological Reviews 2009, vol. 228:149-169.

Gleixner et al., "KIT-D816V-independent oncogenic signaling in neoplastic cells in systemic mastocytosis: role of Lyn and Btk activation and disruption by dasatinib and bosutinib", Blood. Aug. 18, 2011;118(7):1885-1898.

Georgin-Lavialle et al., "Mast cell leukemia: identification of a new c-Kit mutation, dup(501-502), and response to masitinib, a c-Kit tyrosine kinase inhibitor", European Journal of Haematology, Jul. 2012;89(1):47-52.

Clinical Trial AB04010—2009, available at https://clinicaltrials.gov/ct2/show/NCT00831974.

Clinical Trial AB06013—2010, available at https://clinicaltrials.gov/ct2/show/NCT01266369.

AB Science Press release—Nov. 10, 2014 available at http://www.ab-science.com/file_bdd/content/1415634498_20141110_Mastocytosis_call_press_release_EN.pd.

\* cited by examiner

TREATMENT OF MASTOCYTOSIS WITH MASITINIB

The present invention relates to the treatment of mastocytosis, and in particular indolent forms of mastocytosis (including smoldering systemic, indolent systemic and cutaneous mastocytosis), comprising administration of masitinib or a pharmaceutically acceptable salt or solvate thereof in an appropriate dosage regimen.

BACKGROUND OF THE INVENTION

Mastocytosis

Mastocytosis (also referred to as mast cell disease) is defined as a clonal, neoplastic proliferation and accumulation of mast cells in one or multiple organs. Clinical signs and symptoms result from the release of chemical mediators and by infiltration of tissues (e.g., bone marrow, spleen, lymph nodes, liver, and gastrointestinal tract) by neoplastic mast cells. Mast cells are bone marrow derived cells that produce histamine and other substances causing allergic and anaphylactic reactions. Accumulation of mast cells in body organs can inhibit the functionality of the organ and eventually cause degeneration. Mastocytosis usually involves the skin and bone marrow, but may also involve other internal organs.

Diagnosis and Classification of Mastocytosis

Clinical advances have cumulated in development of the World Health Organization (WHO) consensus classification system for mastocytosis (Table 1) (Horny H P et al., in World Health Organization Classification of Tumours. Pathology and Genetics of Tumours of Haematopoietic and Lymphoid Tissues. Lyon, France: IARC Press; 2008. pp 54-63; or Arock, et al. Eur J Haematol. 2015 June; 94(6):474-90). Based upon clinical findings and symptoms, seven major categories of mastocytosis patients have been identified: cutaneous mastocytosis (CM) and six main variants of systemic mastocytosis (SM): indolent SM, SM with associated clonal hematological nonmast-cell lineage disease (SM-AHNMD), aggressive SM, mast cell leukemia, mast cell sarcoma, and extracutaneous mastocytoma. Prognosis relates to the SM variant and extends from a normal life expectancy in CM or indolent SM, to only a few months in mast cell leukemia (Valent P, et al., Br J Haematol 2003; 122:695-717).

A further possible distinction of mastocytosis based on WHO consensus classification system is as follows:

indolent forms of mastocytosis which are selected from smoldering systemic (SSM), indolent systemic (ISM) and cutaneous mastocytosis (CM), each being as defined in the WHO consensus classification system for mastocytosis; and aggressive forms of mastocytosis which are selected from aggressive systemic mastocytosis (ASM), systemic mastocytosis associated with another clonal hematological non-mast cell lineage disease (SM-AHNMD), mast cell leukemia (MCL), mast cell sarcoma (MCS), and extracutaneous mastocytoma, each being as defined in the WHO consensus classification system for mastocytosis.

TABLE 1

Official WHO classification (Horny HP et al., in World Health Organization Classification of Tumours. Pathology and Genetics of Tumours of Haematopoietic and Lymphoid Tissues. Lyon, France: IARC Press; 2008).

| Abbreviations | WHO terms | Diagnostic |
|---|---|---|
| CM | Cutaneous Mastocytosis | Typical skin lesions: either maculopapular, urticaria pigmentosa, mastocytoma. Typical infiltrate of mast cell in skin (no other tissue involvement) |
| ISM | Indolent Systemic Mastocytosis | Mast cell infiltration in at least 1 extracutaneous tissue. No B and C Findings |
| SSM | Smoldering Systemic Mastocytosis | Mast cells in bone marrow >5%. At least two B-Findings. No C-Finding |
| SM-AHNMD | Systemic Mastocytosis with an Associated clonal Hematologic Non Mast cell lineage Disease | Associated with myelodysplasia and myeloproliferative syndrome and sometimes with an acute leukemia or lymphoma |
| ASM | Aggressive Systemic Mastocytosis | At least one C-Finding |
| MCL | Mast Cell Leukemia | Large numbers of atypical mast cells in the peripheral blood. Mast cells in bone marrow smears (≥20%). |
| MCS | Mast Cell Sarcoma Extracutaneous Mastocytoma | |

In most of these categories (CM, ISM, SM-AHNMD, ASM, MCL), subvariants have been identified, based on clinical and/or biological features [for example, see Table 1 of Arock, et al. Eur J Haematol. 2015 June; 94(6):474-90]. WHO has also provided diagnostic criteria, with further categorization according to the presence of B-('Borderline Benign') findings and C-('Consider Cytoreduction') findings, which reflect the disease burden (B) and disease aggressiveness (C), respectively [for example, see Tables 2 and 3 of Arock, et al. Eur J Haematol. 2015 June; 94(6): 474-90]. For example, patients who have one or more C-findings are categorized as ASM or MCL and are candidates for therapeutic cytoreduction. Variants on the WHO diagnostic criteria are also used as appropriate.

The WHO diagnostic criterion for SM requires confirmation of one major and one minor criterion, or three minor criteria from a list of specific diagnostic findings (Table 2). The major criterion requires identification of multifocal dense infiltrates of mast cells in the marrow or other extracutaneous organ; minor criteria include: (1) spindle shaped or atypical morphology of mast cells, (2) detection of the D816V c-Kit mutation, (3) mast cell expression of CD2 and/or CD25 in addition to normal mast cell markers (e.g., tryptase and CD117), and (4) a serum tryptase level >20 ng/ml in the absence of another myeloid disorder. More indolent forms of SM are characterized by "B" findings (e.g., organ involvement without dysfunction) and can be distinguished from aggressive subtypes categorized by "C" or clinical findings associated with organ dysfunction. Cytoreductive therapies are usually reserved for patients with "C" findings, or for patients with mediator symptoms causing substantial morbidity and refractory to standard medications such as antihistamines, leukotriene antagonists, and mast cell stabilizers.

TABLE 2

Biological and Clinical Findings as per WHO definition (Horny HP et al., in World Health Organization Classification of Tumours. Pathology and Genetics of Tumours of Haematopoietic and Lymphoid Tissues. Lyon, France: IARC Press; 2008).

| B findings | C findings |
| --- | --- |
| High Mast Cell burden: Infiltration grade in bone marrow (bm) > 30% by histology and/plus serum tryptase >200 ng/ml. Dysmyelopoiesis: Hypercellular marrow with loss of fat cells or discrete signs of Myelodysplasia or Myeloproliferation, normal blood counts or slight persisting deviation without progression. Organomegaly: Palpable Hepatomegaly without ascites or other signs of organ impairment or/and Lymphadenopathy palpable or visceral LN-enlargement found in US or CT (>2 cm) and/or Palpable Splenomegaly without hypersplenism. | Organopathies Bone Marrow: cytopenia ANC <1 000/µL Hb <10 g/dl Plt <100 00/µL (one or more found). Liver: palpable Hepatomegaly with ascites, abnormal liver function tests and/or portal hypertension. Spleen: palpable splenomegaly with hypersplenism. GI tract: malabsorption with hypoalbuminemia and weight loss. Skeleton: bone lesions with large-sized osteolyses or/and severe osteoporosis with consecutive pathologic fractures. |

CM is characterized by the presence of skin lesions in the absence of bone marrow or other internal organ infiltration by mast cells. In contrast to systemic mastocytosis, there are no well-defined pathologic criteria for diagnosis of CM. Diagnosis is generally established by observation of typical lesions of urticaria pigmentosa or mastocytoma, and by skin biopsies showing increased numbers of mast cells in the absence of other inflammatory cells, particularly in the upper dermis around blood vessels.

The aggressive forms of mastocytosis are rare (<10% of all cases) and require specific treatment aimed at reducing mast cell infiltration and activity. In the vast majority of cases (>90%), mastocytosis presents as an indolent form of the disease, e.g., smoldering SM, indolent SM or CM.

Role of Mast Cells in Inflammation

Mast cells are characterized by their heterogeneity, not only regarding tissue location and structure but also at functional and histochemical levels. Mast cell activation is followed by the controlled release of a variety of mediators that are essential for the defense of the organism against invading pathogens. By contrast, in the case of hyperactivation of mast cells, uncontrolled hypersecretion of these mediators is deleterious for the body. Mast cells produce a large variety of mediators categorized here into three groups:

Preformed granule-associated mediators (histamines, proteoglycans, and neutral proteases);

Lipid-derived mediators (prostaglandins, thromboxanes and leucotrienes);

Various cytokines (including the interleukins: IL-1, IL-2, IL-3, IL-4, IL-5, IL-6, IL-8 and tumor necrosis factor alpha TNF-α, GM-CSF, MIP-1α, MIP-1β and IFN-γ).

Human mast cells constitutively express a number of receptors for different biological molecules. Among these receptors, whose ligation induces the activation of mast cells, the best known is the high affinity receptor for IgE (FcεRI). Binding of IgE-multivalent antigen complexes to FcεRI leads to receptor aggregation and internalization, signaling, and degranulation. This can be accompanied by the transcription of cytokine genes, thus, perpetuating the inflammatory response. Moreover, triggering of mast cells leads to the secretion of diverse pre-formed and/or de novo synthesized mediators, such as vasoactive amines (histamine, serotonin), sulfated proteoglycans, lipid mediators (prostaglandin D2, leucotrienes), growth factors, proteases, cytokines and chemokines as described previously. These mediators can, alone or in synergy with macrophage-derived and T cell-derived cytokines, generate a complex inflammatory response and induce the recruitment and activation of inflammatory cells to the site of degranulation.

Treatment of Mastocytosis

The treatment of mastocytosis, and in particular the long-term management of indolent forms of mastocytosis, remains a challenge to clinicians because of the diversity and complexity of the disease itself and the lack of a standard and highly effective therapy. None of these approved drugs represent a cure for the disease, no therapy available effectively destroys the mast cells responsible for mastocytosis; moreover, their efficacy is limited and may decrease over time, with undesirable side effects reported. In general, management of patients within all categories of mastocytosis includes: (i) avoidance of factors triggering acute mediator release, (ii) symptomatic treatment of acute mast cell mediator release, (iii) treatment of chronic mast cell mediator release, and if indicated (iv) an attempt to treat organ infiltration by mast cells. However, even with the help of appropriate symptomatic treatments, indolent forms of mastocytosis can have a profoundly negative impact on quality of life, with many of the symptoms and their associated disabilities often being unrecognized as manifestations of mastocytosis for several years.

In a recent retrospectively studied of Mayo Clinic patients who met the 2008 WHO diagnostic criteria for SM and had received at least one of four major cytoreductive drugs including: interferon-alpha with or without prednisone (IFN-α), hydroxyurea (HU), imatinib mesilate (IM) or Cladribine (2-CdA), were evaluated for response (Kim et al., Am J Hemato. 2009; 84:790-4). The corresponding overall response rates for those patients with indolent SM (N=22) were 60%, 0%, 14%, and 56%, respectively. Considering the entire evaluable study population (N=108), which included patients with more aggressive forms of mastocytosis such as aggressive SM, SM associated with another clonal hematological nonmast cell lineage disease (SM-AHNMD), and mast cell leukemia, the corresponding overall (and major) response rates were 53% (18%), 19% (0%), 18% (9%), and 55% (37%), respectively. Although the major response rates with these four cytoreductive agents were still suboptimal, the study concluded that 2-CdA and IFN-α constitute the treatments of choice, at the present time, for first line therapy in SM. It was noted however, that the degree and duration of response from these drugs remained inadequate and novel drugs are required to address this unmet need.

Interferon therapy has been used in mastocytosis because of its activity in myeloproliferative disorders. A few reports based on small series of patients have suggested that interferon therapy may induce some responses in the disease, even in some cases complete response. However, it has also been shown that interferon therapy cannot reduce mast cell infiltration in most cases. Furthermore, in mastocytosis interferon therapy is associated with a high rate of side effects and particularly with depression. As a consequence the dropout rate is very high and only few patients (>25%) can maintain therapy for a long period of time. A few cases suggest that corticosteroids and interferon together may improve response rate; however, corticosteroids are also associated with side effects. Thus, interferon with or without prednisone may be used in mastocytosis to reduce mast cell mediator release symptoms but its potential benefits must be weighed against its high rate of side effects.

Cladribine (Leustatin®) is a purine analogue that is efficient to induce apoptosis in resting cells. It has been used successfully in hairy cell leukemia and in Langerhans histiocytosis. Recent publications showed 2-CdA to effectively decrease symptoms associated with mediators release and also to reduce mast cell tumor burden in up to 50% of cases with few complete responses. However, relapses occur and maintenance therapy is probably needed in the majority of cases. Although well tolerated, 2-CdA administration induces an immunosuppressive state and although not yet fully demonstrated is potentially carcinogenic. Therefore, the feasibility of 2-CdA treatment in the long-term maintenance therapy of indolent mastocytosis is questionable.

The identification and prevalence of the D816V c-Kit tyrosine kinase mutation in mastocytosis has led to development of novel drugs directed against mast cells. Imatinib was the first of a new class of drugs known as small molecular weight tyrosine kinase inhibitors capable of blocking tyrosine kinase activity of c-Kit. In vitro experiments, however, showed that mast cells carrying the D816V c-Kit mutation were resistant to imatinib. Nevertheless, imatinib has been administered to mastocytosis patients with limited success in SM, although better response has been observed in rare cases of mastocytosis with transmembrane c-Kit mutations. Recently, a study by Vega Ruiz et al. (Leuk Res 2009; 33:1481-1484) showed that 6/11 indolent mastocytosis patients reported symptomatic improvements while receiving imatinib therapy, two of whom had the c-Kit D816V mutation. However, response was relatively short-lived, all patients developing resistance with reoccurrence of symptoms, leading to a conclusion that imatinib therapy did not result in appreciable clinical activity in patients with c-Kit D816V mutation. This unsatisfactory level of efficacy was confirmed in the Mayo Clinic retrospectively study (Kim et al., Am J Hemato. 2009; 84:790-4), with imatinib demonstrating a low overall response rate of 17% in c-Kit D816V positive SM patients, leading to the authors not endorsing the use of imatinib in patients with WHO-defined SM. Moreover, imatinib has shown cardiotoxicity related to its inhibition of the Abelson kinase (ABL), making its long-term use questionable for treatment of indolent forms of mastocytosis. In contrast to imatinib, a newer generation of tyrosine inhibitors dasatinib and midostaurin (PKC412) can inhibit the constitutive activity of the c-Kit D816V tyrosine kinase. However, when tested in vivo these drugs have also not lived-up to expectations, as seen in a phase 2 study that concluded dasatinib does not eliminate SM in the patients with c-Kit D816V mutation (Verstovsek et al., Clin Cancer Res. 2008; 14:3906-15).

There exists a continuing need to identify new targeted drugs that possess greater inhibitory action against c-Kit, with improved selectivity to minimize side effects, capable of inhibiting mast cell survival and release of mast cell mediators for treatment of mastocytosis with mast cell mediator release associated handicap, and in particular indolent forms of mastocytosis. In the absence of any single drug achieving a widespread response, it is possible that combination therapy based on different cytoreductive or disease modifying drugs may also be a viable strategy for both indolent forms and aggressive forms of mastocytosis.

AIMS OF THE INVENTION

The invention aims to solve the technical problem of providing an active ingredient for the treatment of mastocytosis with mast cell mediator release associated handicap, and in particular either one or more of cutaneous mastocytosis (CM), indolent systemic mastocytosis (ISM) or smoldering systemic mastocytosis (SSM).

The invention also relates to the treatment of such a disease in a human patient, regardless of said patient's c-Kit D816V mutation status; that is to say, for patients who are classified as either c-Kit D816V positive or c-Kit D816V negative.

The invention aims to provide an efficient treatment for such a disease at an appropriate dose, route of administration and daily intake.

The invention also aims to solve the technical problem of providing an active ingredient that improves prior art methods for the treatment of mastocytosis.

SUMMARY OF THE INVENTION

In one embodiment the present invention relates to the use of a tyrosine kinase inhibitor or a mast cell inhibitor or a pharmaceutically acceptable salt or solvate thereof, especially masitinib or a pharmaceutically acceptable salt or solvate thereof, for the preparation of a medicament for the treatment of mastocytosis, and in particular cutaneous or systemic mastocytosis, in human subjects or patients, wherein said tyrosine kinase inhibitor or mast cell inhibitor or a pharmaceutically acceptable salt or solvate thereof is to be administered to patients in need thereof, optionally combined with at least one other cytoreductive or disease modifying drug, and wherein said patients optionally suffer from mast cell mediator release associated handicap with an overall patient assessment (OPA) ≥1.

The term "subject" refers to a mammal, preferably a human. In one embodiment, a subject may be a "patient", i.e. a warm-blooded animal, more preferably a human, who/ which is awaiting the receipt of, or is receiving medical care or was/is/will be the object of a medical procedure, or is monitored for the development of mastocytosis.

The terms "treating" or "treatment" refers to both therapeutic treatment and prophylactic or preventative measures; wherein the object is to prevent or slow down (lessen) mastocytosis. Those in need of treatment include those already with mastocytosis as well as those prone to have mastocytosis or those in whom mastocytosis is to be prevented. A subject is successfully "treated" for mastocytosis if, after receiving a therapeutic amount of a tyrosine kinase inhibitor according to the methods of the present invention, the subject shows observable and/or measurable reduction in or absence of one or more of the following: reduction in the number of pathogenic cells; reduction in the percent of total cells that are pathogenic; and/or relief to some extent, of one or more of the symptoms associated with mastocytosis; reduced morbidity and mortality, and improvement in quality of life issues. The above parameters for assessing successful treatment and improvement in the disease are readily measurable by routine procedures familiar to a physician.

In one embodiment, a therapeutically acceptable amount of a tyrosine kinase inhibitor or a mast cell inhibitor or a pharmaceutically acceptable salt or solvate thereof, especially masitinib or a pharmaceutically acceptable salt or solvate thereof is administered to the subject.

The term "therapeutically effective amount" means the level or amount of agent that is aimed at, without causing significant negative or adverse side effects to the target, (1) delaying or preventing the onset of mastocytosis; (2) slowing down or stopping the progression, aggravation, or deterioration of one or more symptoms of mastocytosis; (3) bringing about ameliorations of the symptoms of mastocytosis; (4) reducing the severity or incidence of mastocytosis; or (5) curing mastocytosis. A therapeutically effective amount may be administered prior to the onset of mastocytosis, for a prophylactic or preventive action. Alternatively or additionally, the therapeutically effective amount may be administered after initiation of mastocytosis, for a therapeutic action or maintenance of a therapeutic action.

In one embodiment the present invention relates to a method of treatment of mastocytosis, and in particular cutaneous or systemic mastocytosis, in human patients, wherein a tyrosine kinase inhibitor or a mast cell inhibitor or a pharmaceutically acceptable salt or solvate thereof, especially masitinib or a pharmaceutically acceptable salt or solvate thereof, is to be administered in patients in need thereof, optionally combined with at least one other cytoreductive or disease modifying drug, and wherein said patients optionally suffer from mast cell mediator release handicap with an overall patient assessment (OPA) ≥1.

In one embodiment the present invention relates to the use or the method as defined above wherein said patients are those afflicted by mastocytosis with mast cell mediator release associated handicap of mild disability to those with intolerable disability; more specifically with OPA scores of between: 1 to 4 (mild disability to intolerable disability), or 2 to 4 (moderate disability to intolerable disability), or even 3 to 4 (severe disability to intolerable disability).

In one embodiment the present invention relates to the use or the method as defined above wherein said patients' handicapped status is defined as presenting with at least two of the following mast cell mediator release associated handicaps, including at least one among pruritus, flushes, depression, or asthenia, with individual handicaps defined as: pruritus score ≥6; number of flushes per week ≥7; Hamilton rating scale (depression) ≥10; number of stools per day ≥4; number of micturitions per day ≥8; Fatigue Impact Scale total score (asthenia) ≥40.

In one embodiment the present invention relates to the use or the method as defined above wherein said patients' handicapped status is defined as severe (i.e. mastocytosis is severe mastocytosis), i.e. as presenting with at least one, preferably 2, 3 or 4 of the following mast cell mediator release associated handicaps: pruritus score ≥9; number of flushes per week ≥8; depression measured by the Hamilton rating scale ≥19; and asthenia (fatigue) with a fatigue score measured by Fatigue Impact Scale (FIS) ≥75 or any equivalent cut-off determined using the FSS, FSI, BFI or MAF.

In one embodiment the present invention relates to a method for treating severe systemic mastocytosis in human patients comprising administering a tyrosine kinase inhibitor or a pharmaceutically acceptable salt or solvate thereof, wherein said severe mastocytosis is associated with at least two of the six following mast cell mediator release associated handicaps: a pruritus score ≥9; a number of flushes per week ≥8; a Hamilton rating scale for depression (HAMD-17) score ≥19; a number of stools per day ≥4; a number of micturition per day ≥8; a fatigue score (asthenia) measured by Fatigue Impact Scale ≥75, wherein at least one handicap is selected among pruritus, flushes, depression and fatigue. (asthenia).

In one embodiment, said severe mastocytosis, preferably severe systemic mastocytosis, is associated with at least two mast cell mediator release associated handicaps selected from the list comprising pruritus score ≥9; number of flushes per week ≥8; depression measured by the Hamilton rating scale ≥19; fatigue score measured by FIS ≥75; number of stools per day ≥4 and number of micturition per day ≥8, wherein preferably at least one mast cell mediator release associated handicap is selected from the list comprising pruritus score ≥9; number of flushes per week ≥8; depression measured by the Hamilton rating scale ≥19; fatigue score measured by FIS ≥75, and more preferably wherein at least one mast cell mediator release associated handicap is selected from the list comprising pruritus score ≥9 and number of flushes per week ≥8.

In one embodiment, said severe mastocytosis, preferably severe systemic mastocytosis, is associated with at least one severe mast cell mediator release associated handicap selected from the list comprising: pruritus score ≥9, number of flushes per week ≥8, depression measured by the Hamilton rating scale ≥19, fatigue score measured by FIS ≥75.

In one embodiment, said severe mastocytosis, preferably severe systemic mastocytosis, is associated with at least one mast cell mediator release associated handicap selected from the list comprising pruritus score ≥9 and number of flushes per week ≥8. In one embodiment, said severe systemic mastocytosis is associated with pruritus score ≥9 and number of flushes per week ≥8.

In one embodiment, said severe mastocytosis, preferably severe systemic mastocytosis, is associated with at least two mast cell mediator release associated handicaps selected from the list comprising pruritus score ≥9; number of flushes per week ≥8; and depression measured by the Hamilton rating scale ≥19.

In one embodiment, said severe mastocytosis, preferably severe systemic mastocytosis, is associated with the three mast cell mediator release associated handicaps: pruritus score ≥9; number of flushes per week ≥8; and depression measured by the Hamilton rating scale ≥19.

In one embodiment, said severe mastocytosis, preferably severe systemic mastocytosis, is associated with the four mast cell mediator release associated handicaps: pruritus score ≥9; number of flushes per week ≥8; depression measured by the Hamilton rating scale ≥19 and asthenia (fatigue) with a fatigue score measured by Fatigue Impact Scale (FIS) ≥75 or any equivalent cut-off determined using the FSS, FSI, BFI or MAF.

In one embodiment, said severe mastocytosis, preferably severe systemic mastocytosis, is associated with asthenia (fatigue) with a fatigue score measured by Fatigue Impact Scale (FIS) ≥75 or any equivalent cut-off determined using the FSS, FSI, BFI or MAF.

In one embodiment the present invention relates to the use or the method as defined above wherein said tyrosine kinase inhibitor or a mast cell inhibitor or a pharmaceutically acceptable salt or solvate thereof, especially masitinib or a pharmaceutically acceptable salt or solvate thereof, is to be administered for the treatment of cutaneous mastocytosis, and in particular cutaneous mastocytosis with mast cell mediator release associated handicap.

In one embodiment the present invention relates to the use or the method as defined above wherein said tyrosine kinase inhibitor or a mast cell inhibitor or a pharmaceutically acceptable salt or solvate thereof, especially masitinib or a pharmaceutically acceptable salt or solvate thereof, is to be administered for the treatment of systemic mastocytosis, and in particular systemic mastocytosis with mast cell mediator release associated handicap, preferably severe systemic mastocytosis as described hereinabove.

In one embodiment the present invention relates to the use or the method as defined above for treating systemic mastocytosis (such as, for example, indolent systemic mastocytosis and smoldering systemic mastocytosis), preferably severe systemic mastocytosis, wherein severe mastocytosis corresponds to patients with a handicap status defined as severe, i.e. as presenting with at least one, preferably 2, 3 or 4 of the following mast cell mediator release associated handicaps: pruritus score ≥9; number of flushes per week ≥8; depression measured by the Hamilton rating scale ≥19; and asthenia (fatigue) with a fatigue score measured by Fatigue Impact Scale (FIS) ≥75 or any equivalent cut-off determined using the FSS, FSI, BFI or MAF.

According to an embodiment, said systemic form of mastocytosis is defined by the World Health Organization (WHO) classification and diagnostic criteria [Arock M, et al. Eur J Haematol. 2015 June; 94(6):474-90], or said systemic form of mastocytosis is defined using two modified diagnostic criteria, referred to hereafter as the 'AB Science Systemic Mastocytosis (ABSSM) criteria', or as the 'Protocol AB06006 v7 criteria', as defined herein below.

In a first embodiment, "systemic mastocytosis" corresponds to the mastocytosis subpopulations of indolent systemic mastocytosis and smoldering systemic mastocytosis, as defined according to the World Health Organization (WHO) diagnostic criteria [Arock M, et al. *Eur J Haematol.* 2015 June; 94(6):474-90]. A diagnosis of systemic mastocytosis is made according to the presence of B-('Borderline Benign') findings and C-('Consider Cytoreduction') findings, which reflect the disease burden (B) and disease aggressiveness (C), respectively. Patients who have systemic mastocytosis without B- or C-findings and without signs of an associated clonal hematologic non-mast cell lineage disease (AHNMD) are diagnosed as "indolent systemic mastocytosis" (ISM). Patients who have two or more B-findings, but no C-findings, are diagnosed with "smoldering systemic mastocytosis" (SSM), a separate systemic mastocytosis category initially considered a subtype of ISM defined by a huge mass of neoplastic mast cells.

In a second embodiment, "systemic mastocytosis" corresponds to the mastocytosis subpopulation as defined according to the AB Science Systemic Mastocytosis (ABSSM) diagnostic criteria, and thus relates to a disease for which any the following four criteria are fulfilled at baseline or before baseline:

Presence of mast cells in any bone marrow biopsy or aspirate associated with at least one sign of abnormality, wherein said abnormal signs are:
More than 1% infiltration of mast cells in bone marrow.
Aggregates of more than 15 mast cells in bone marrow that can be described by the following words: nodules, seats, clusters, foci, or granuloma.
More than 25% atypical mast cells in a sample of bone marrow.
Abnormal mast cells in the sample of bone marrow with microscopic testing that can be described by the following words: spindled, abnormal, atypical, fusiform, dystrophic, pathologic, dysmorphic.
Abnormal immunohistochemistry signs: mast cells in bone marrow express CD2 and/or CD25 present.
c-Kit point mutation at codon 816 (c-Kit 816) in bone marrow.
Detection of c-Kit 816 in bone marrow without evidence of mast cells in bone marrow and detection of c-Kit 816 in skin biopsy justifying clonality.
Presence of mast cells in bone marrow biopsy or aspirate without signs of mast cell abnormality.
Excess of mast cells detected in digestive organs in addition to excess of mast cells in the skin.

In a third embodiment, the term systemic mastocytosis is defined by the Protocol AB06006 version 7.0 (v7) diagnostic criteria and thus relates to a disease for which the following criteria are fulfilled:

Patient with one of the following documented mastocytosis as per WHO classification:
Smoldering Systemic Mastocytosis;
Indolent Systemic Mastocytosis; and/or
Patient with documented mastocytosis and evaluable disease based upon histological criteria including typical infiltrates of mast cells in a multifocal or diffuse pattern in skin and/or bone marrow biopsy.

In one embodiment, said severe systemic mastocytosis is smoldering systemic mastocytosis or indolent systemic mastocytosis.

In one embodiment said systemic mastocytosis, preferably said severe systemic mastocytosis, is associated with at least one (in particular associated with 1, or with 2, or with 3 or with 4) mast cell mediator release associated handicap(s) selected from the list comprising pruritus score ≥9; number of flushes per week ≥8; depression measured by the Hamilton rating scale ≥19; and asthenia (fatigue) with a fatigue score measured by Fatigue Impact Scale (FIS) ≥75 or any equivalent cut-off determined using the FSS, FSI, BFI or MAF, preferably wherein at least one mast cell mediator release associated handicap is pruritus score ≥9; number of flushes per week ≥8.

In one embodiment said systemic mastocytosis, preferably said severe systemic mastocytosis, is associated with at least one, preferably at least two, mast cell mediator release associated handicap(s) selected from the list comprising pruritus score ≥9; number of flushes per week ≥8; and depression measured by the Hamilton rating scale ≥19. In another embodiment said systemic, preferably said severe systemic mastocytosis, mastocytosis is associated with the three following mast cell mediator release associated handicaps: pruritus score ≥9; number of flushes per week ≥8; and depression measured by the Hamilton rating scale ≥19.

In one embodiment the present invention relates to the method as defined above, wherein said tyrosine kinase inhibitor or a pharmaceutically acceptable salt or solvate thereof is an inhibitor of wild-type c-Kit, Lyn and Fyn kinase activity.

In one embodiment the present invention relates to the use or the method as defined above wherein tyrosine kinase inhibitor or a pharmaceutically acceptable salt or solvate thereof is masitinib or a pharmaceutically acceptable salt or solvate thereof.

In one embodiment the present invention relates to the use or the method as defined above wherein masitinib or a pharmaceutically acceptable salt or solvate thereof is masitinib mesilate.

In one embodiment the present invention relates to the use or the method as defined above wherein a tyrosine kinase inhibitor or a mast cell inhibitor or a pharmaceutically acceptable salt or solvate thereof, especially masitinib or a pharmaceutically acceptable salt or solvate thereof, is an inhibitor of wild-type c-Kit and/or Lyn or Fyn kinase activity but inactive against the D816V mutation of c-Kit, and wherein said mastocytosis patients are classified as either c-Kit D816V positive or c-Kit D816V negative.

In another embodiment, said tyrosine kinase inhibitor or a pharmaceutically acceptable salt or solvate thereof, especially masitinib or a pharmaceutically acceptable salt or solvate thereof is administered at a dose of 1.5, 3.0, 4.5, 6.0, 7.5, or 9.0 mg/kg/day (mg per kilo body weight per day).

In one embodiment the present invention relates to the use or the method as defined above wherein masitinib or a pharmaceutically acceptable salt or solvate thereof is to be administered at a starting daily dose of 3.0 to 6.0 mg/kg/day, with the preferred embodiment for patients with indolent mastocytosis with mast cell mediator release associated handicap being a starting daily dose of 4.5 to 6.0 mg/kg/day.

In one embodiment the present invention relates to the use or the method as defined above wherein masitinib or a pharmaceutically acceptable salt or solvate thereof is dose escalated by increments of 1.5 mg/kg/day to reach a maximum of 9.0 mg/kg/day.

In one embodiment the invention, said tyrosine kinase inhibitor or mast cell inhibitor or a pharmaceutically acceptable salt or solvate thereof, especially masitinib or a pharmaceutically acceptable salt or solvate thereof, is initially administered at a dose of 3.0 mg/kg/day during at least 4 weeks, then 4.5 mg/kg/day during at least 4 weeks, and at 6 mg/kg/day thereafter, with each dose escalation being subjected to toxicity controls.

In one embodiment the present invention relates to the use or the method as defined above wherein patients are those afflicted with mastocytosis with mast cell mediator release associated handicap, and in particular cutaneous or systemic mastocytosis, wherein said patients have a positive D816V c-Kit mutation status.

In one embodiment the present invention relates to the use or the method as defined above wherein patients are those afflicted with mastocytosis with mast cell mediator release associated handicap, and in particular cutaneous or systemic mastocytosis, wherein said patients have a negative D816V c-Kit mutation status.

In one embodiment the present invention relates to the use or the method as defined above wherein patients are those afflicted with mastocytosis with mast cell mediator release associated handicap, and in particular cutaneous or systemic mastocytosis, wherein said patients have a mixed c-Kit mutation status defined as both positive and negative D816V c-Kit mutation status with mast cell infiltrated organs.

In one embodiment the present invention relates to the use or the method as defined above wherein said tyrosine kinase inhibitor or mast cell inhibitor or a pharmaceutically acceptable salt or solvate thereof, especially masitinib or a pharmaceutically acceptable salt or solvate thereof, is administered orally.

In one embodiment the present invention relates to the use or the method as defined above wherein said tyrosine kinase inhibitor or mast cell inhibitor or a pharmaceutically acceptable salt or solvate thereof, especially masitinib or a pharmaceutically acceptable salt or solvate thereof, is administered twice a day (i.e. in two daily intakes).

In one embodiment the present invention relates to the use or the method as defined above comprising a long-term administration of an effective amount of said tyrosine kinase inhibitor or mast cell inhibitor or a pharmaceutically acceptable salt or solvate thereof, especially masitinib or a pharmaceutically acceptable salt or solvate thereof, over more than 3 months, preferably more than 12 months.

In one embodiment the present invention relates to the use or the method as defined above wherein the said tyrosine kinase inhibitor or a pharmaceutically acceptable salt or solvate thereof, is comprised in a pharmaceutical composition in an amount of at least 50 mg and less than 600 mg, preferably of at least 100 mg and less than 400 mg.

In one embodiment the present invention relates to the use or the method as defined above wherein the said pharmaceutical composition comprises a dose of at least 50 mg and less than 150 mg, and preferably of 100 mg, of said tyrosine kinase inhibitor or mast cell inhibitor or a pharmaceutically acceptable salt or solvate thereof, especially masitinib or a pharmaceutically acceptable salt or solvate thereof.

In one embodiment the present invention relates to the use or the method as defined above wherein the said pharmaceutical composition comprises a dose of at least 150 mg and less than 400 mg, and preferably of 200 mg, of said tyrosine kinase inhibitor or mast cell inhibitor or a pharmaceutically acceptable salt or solvate thereof, especially masitinib or a pharmaceutically acceptable salt or solvate thereof.

In one embodiment the present invention relates to the use or the method as defined above wherein the tyrosine kinase inhibitor or a mast cell inhibitor or a pharmaceutically acceptable salt or solvate thereof, especially masitinib or a pharmaceutically acceptable salt or solvate thereof, is administered for the treatment of indolent mastocytosis with mast cell mediator release associated handicap, and in particular cutaneous or systemic mastocytosis, in combination with at least one other cytoreductive or disease modifying drug.

In one embodiment the present invention relates to the use or the method as defined above wherein the tyrosine kinase inhibitor or a mast cell inhibitor or a pharmaceutically acceptable salt or solvate thereof, especially masitinib or a pharmaceutically acceptable salt or solvate thereof, is administered for the treatment of aggressive forms of mastocytosis with mast cell mediator release associated handicap, and in particular Systemic Mastocytosis with an Associated clonal Hematologic Non Mast cell lineage Disease, Aggressive Systemic Mastocytosis, Mast Cell Leukemia, Mast Cell Sarcoma, or Extracutaneous Mastocytoma, in combination with at least one other cytoreductive or disease modifying drug.

In one embodiment the present invention relates to the use or the method as defined above wherein the second cytoreductive or disease modifying drug is selected from the group consisting of: interferon-alpha (IFN-α); cladribine (2-CdA); hydroxyurea; a c-Kit kinase inhibitor, including imatinib, dasatinib or midostaurin (PKC412); and any combination of these cytoreductive or disease modifying drugs.

In one embodiment the present invention relates to the use or the method as defined above wherein said tyrosine kinase inhibitor or mast cell inhibitor or a pharmaceutically acceptable salt or solvate thereof, especially masitinib or a pharmaceutically acceptable salt or solvate thereof, and one or more cytoreductive or disease modifying drugs are to be administered separately, simultaneously or sequentially in time.

In one embodiment the present invention relates a tyrosine kinase inhibitor or a mast cell inhibitor or a pharmaceutically acceptable salt or solvate thereof, especially masitinib or a pharmaceutically acceptable salt or solvate thereof, for use as a medicament or in a pharmaceutical composition for a method as defined above.

In one embodiment the invention relates to a tyrosine kinase inhibitor or a mast cell inhibitor or a pharmaceutically acceptable salt or solvate thereof, especially masitinib or a pharmaceutically acceptable salt or solvate thereof, for the treatment of mastocytosis, and in particular to patients with WHO-defined cutaneous or systemic mastocytosis, in human patients, wherein masitinib is to be administered daily at a starting dose of 3.0 to 6.0±1.5 mg/kg/day and wherein said patients suffer from mast cell mediator release associated handicap with an overall patient assessment (OPA) ≥1.

In one embodiment the invention also relates to a method of treatment of mastocytosis, and in particular according to the WHO-defined cutaneous or systemic mastocytosis, in human patients, wherein a tyrosine kinase inhibitor or a mast cell inhibitor or a pharmaceutically acceptable salt or solvate thereof, especially masitinib or a pharmaceutically acceptable salt or solvate thereof, is to be administered daily at a starting dose of 3.0 to 6.0±1.5 mg/kg/day, and wherein said patients suffer from mast cell mediator release handicap with an overall patient assessment (OPA) ≥1.

In one embodiment, the invention relates to a method of treatment of mastocytosis, in human patients with mast cell mediator release associated handicap, wherein a tyrosine kinase inhibitor or a mast cell inhibitor or a pharmaceutically acceptable salt or solvate thereof, especially masitinib or a pharmaceutically acceptable salt or solvate thereof, is an inhibitor of wild-type c-Kit and/or Lyn or Fyn kinase activity but inactive against the D816V mutation of c-Kit, and wherein said patients are classified as either c-Kit D816V positive or c-Kit D816V negative.

In one embodiment, said mastocytosis is systemic mastocytosis, preferably severe systemic mastocytosis.

In another embodiment, the invention also relates to a method of treatment of mastocytosis, in human patients with mast cell mediator release associated handicap, wherein a tyrosine kinase inhibitor or a mast cell inhibitor or a pharmaceutically acceptable salt or solvate thereof, especially masitinib or a pharmaceutically acceptable salt or solvate thereof, is administered for the treatment of mastocytosis in combination with at least one other cytoreductive or disease modifying drug; for example, interferon-alpha (IFN-α), cladribine (2-CdA), hydroxyurea, and c-Kit kinase inhibitors including imatinib, dasatinib or midostaurin (PKC412).

In one embodiment, said mastocytosis is systemic mastocytosis, preferably severe systemic mastocytosis.

The present invention also relates a method for treating severe systemic mastocytosis in human patients, comprising administering a tyrosine kinase inhibitor or a pharmaceutically acceptable salt or solvate thereof, wherein said tyrosine kinase inhibitor is masitinib mesilate and wherein said severe mastocytosis is associated with at least one (including 1, 2, 3 or 4) mast cell mediator release associated handicap(s) selected from the list comprising pruritus score ≥9; number of flushes per week ≥8; depression measured by the Hamilton rating scale ≥19 and asthenia (fatigue) with a fatigue score measured by Fatigue Impact Scale (FIS) ≥75 or any equivalent cut-off determined using the FSS, FSI, BFI or MAF, wherein preferably at least of mast cell mediator release associated handicap is pruritus score ≥9 or number of flushes per week ≥8.

DESCRIPTION OF THE INVENTION

Role of c-Kit in Mastocytosis

Stem cell factor (SCF), the ligand of the c-Kit receptor, is a major growth factor for mast cell survival, proliferation, differentiation, adhesion and degranulation processes (Reber et al., Eur J Pharmacol 2008; 533:327-340), with SCF-dependent activation of c-Kit critical for mast cell homeostasis and function. Binding of SCF to the c-Kit receptor induces c-Kit dimerization followed by its transphosphorylation, leading to the recruitment and activation of various intracytoplasmic substrates. These activated substrates induce multiple intracellular signaling pathways responsible for cell proliferation and activation. The symptoms of mastocytosis are caused by the uncontrolled accumulation of mast cells and release of their mediators. Deregulated activity of the SCF/c-Kit pathway in mastocytosis is related to mutations in the c-Kit receptor. It has been shown that between 70% and 90% of patients with SM carry the gain-of-function Asp-816-Val (D816V) mutation in the kinase (phosphotransferase) domain of c-Kit, with the remainder (10% and 30%) carrying mutations in other domains of the molecule, such as the transmembrane domain. The D816V c-Kit mutation is also found in some patients with CM. This mutation is associated with ligand-independent constitutive activation of c-Kit signaling, leading to uncontrolled mast cell proliferation, resistance to apoptosis and mediator release.

Mast Cell Mediator Release and Mastocytosis with Handicap

The aggressive forms of mastocytosis are rare (<10% of all cases) and require specific treatment aimed at reducing mast cell infiltration and activity. In the vast majority of cases (>90%), mastocytosis presents as an indolent form of the disease, e.g., smoldering SM, indolent SM or CM. Although typically not a life threatening disease, indolent forms of mastocytosis are associated with significant disability in more than 60% of patients. Indeed, patients in all categories of mastocytosis often experience symptoms from the constitutive activation of mast cells and release of their mediators. Collectively, these are referred to as 'mast cell mediator release symptoms' or alternatively as 'mastocytosis with handicap'. Systemic symptoms may include: asthenia, pruritus, food intolerance, erythematous crisis, muscle and joint pain, pollakiuria (micturition frequency), epigastric pain, aerophagia/eructation, memory loss, and psychological impact of the disease, particularly depression (Hermine O, et al., PLoS ONE. 2008; 3:e2266). Each clinical symptom can be objectively measured by frequency or via an appropriate rating scale, although these do not form any part of formal diagnosis of mastocytosis. Global impact of the disease on quality of life can be coarsely evaluated by the overall patient assessment (OPA), for which patients score their mast cell mediator release associated handicap according severity: 0 (no disability), 1 (mild disability), 2 (moderate disability), 3 (severe disability), and 4 (intolerable disability). However, no formally established thresholds for categorizing the burden and severity of disability in mastocytosis related to mast cell mediator release associated handicaps exist. This is in part because the perception of handicap is highly dependent on the patient's lifestyle and environment; that is to say, identical symptoms may be perceived as a handicap resulting in significant detriment to quality-of-life for one patient, yet impact on another patient merely as a minor annoyance. Thus, beyond the WHO's formal diagnosis of mastocytosis and categorization as one of its indolent forms, diagnosis of indolent mastocytosis with mast cell mediator release associated handicap relies upon the patient's and physician's assessment of handicap severity.

To make the patient's and physician's assessment of handicap severity objective and measurable, it is possible to rely on the following measuring methods/rating scales:

for flushes: number of flashes per week;
for diarrhea: number of stools per day;
for pollakiuria: number of number of micturitions per day;
for depression: the score on the Hamilton rating scale (see below for details);
for fatigue: the score on the Fatigue Impact scale (FIS) (see below for details);
for pruritus: the score on an numerically amended version of the scale taught in Hermine O, et al., PLoS ONE. 2008; 3:e2266 (see below for details).

The Hamilton Depression Scale. One of the instruments commonly used to identify depression in patients in clinical trials (including those with mastocytosis) is the 17 items Hamilton Depression Scale (Ham-D17) (Hamilton M. J Neurol Neurosurg Psychiatry. 1960; 23:56-62; Hedlund J L, et al. J Oper Psychiatry. 1979; 10:149-161). The Ham-D17 remains a reference measure to evaluate depression in research concerning somatic patients. Ham-D17 is composed of 17 items scored 0-4 (depressed mood, guilt, suicide, psychic and somatic anxiety, psychomotor retardation, agitation, hypochondriasis, work and interests impairment) or 0-2 (early, middle and late insomnia, gastrointestinal, somatic general, genital, loss of weight and loss of insight items) according to the absence, presence and seriousness of the symptom. An example of a work sheet for calculation of the Hamilton score is shown in table 2a, below:

TABLE 2a

| Activity | Score |
|---|---|
| Depressed mood | |
| Sad, hopeless, helpless, worthless | |
| 0 = Absent | |
| 1 = Gloomy attitude, pessimism, hopelessness | |
| 2 = Occasional weeping | |
| 3 = Frequent weeping | |
| 4 = Patient reports highlight these feelings states in his/her spontaneous verbal and non-verbal communication. | ___ |
| Feelings of guilt | ___ |
| 0 = Absent | |
| 1 = Self-reproach, feels he/she has let people down | |
| 2 = Ideas of guilt or rumination over past errors or sinful deeds | |
| 3 = Present illness is punishment | |
| 4 = Hears accusatory or denunciatory voices and/or experiences threatening visual hallucinations. Delusions of guilt. | |
| Suicide | |
| 0 = Absent | |
| 1 = Feels life is not worth living | |
| 2 = Wishes he/she were dead, or any thoughts of possible death to self | |
| 3 = Suicide, ideas or half-hearted attempt | |
| 4 = Attempts at suicide (any serious attempt rates 4) | ___ |
| Insomnia, early | |
| 0 = No difficulty falling asleep | |
| 1 = Complaints of occasional difficulty in falling asleep i.e. more than half-hour | |
| 2 = Complaints of nightly difficulty falling asleep | ___ |
| Insomnia, middle | |
| 0 = No difficulty | |
| 1 = Patient complains of being restless and disturbed during the night | |
| 2 = Walking during the night - any getting out of bed rates 2 (except voiding bladder) | ___ |
| Insomnia, late | |
| 0 = No difficulty | |
| 1 = Waking in the early hours of the morning but goes back to sleep | |
| 2 = Unable to fall asleep again if he/she gets out of bed | ___ |
| Work and activities | |
| 0 = No difficulty | |
| 1 = Thoughts and feelings of incapacity related to activities: work or hobbies | |
| 2 = Loss of interest in activity - hobbies or work - either directly reported by patient or indirectly seen in listlessness, in decisions and vacillation (feels he/she has to push self to work or activities) | |
| 3 = Decrease in actual time spent in activities or decrease in productivity. In hospital, rate 3 if patient does not spend at leas three hours a day in activities | ___ |

TABLE 2a-continued

| Activity | Score |
|---|---|
| 4 = Stopped working because of present illness. In hospital rate 4 if patient engages in no activities except supervised ward chores | |
| Retardation | |
| Slowness of thought and speech; impaired ability to concentrate; decreased motor activity | |
|     0 = Normal speech and thought | |
|     1 = Slight retardation at interview | |
|     2 = Obvious retardation at interview | |
|     3 = Interview difficult | |
|     4 = Interview impossible | ____ |
| Agitation | |
|     0 = None | |
|     1 = Fidgetiness | |
|     2 = Playing with hands, hair, obvious restlessness | |
|     3 = Moving about; can't sit still | |
|     4 = Hand wringing, nail biting, hair pulling, biting of lips, patient is on the run | ____ |
| Anxiety, psychic | |
| Demonstrated by: | |
|     subjective tension and irritability, loss of concentration | |
|     worrying about minor matters | |
|     apprehension | |
|     fears expressed without questioning | |
|     feelings of panic | |
|     feeling jumpy | |
|     0 = Absent | |
|     1 = Mild | |
|     2 = Moderate | |
|     3 = Severe | |
|     4 = Incapacitating | ____ |
| Anxiety, somatic | |
| Physiological concomitants of anxiety such as: | |
|     gastrointestinal: dry mouth, wind, indigestion, diarrhea, cramps, belching | |
|     cardiovascular: palpations, headaches | |
|     respiratory: hyperventilation, sighing | |
|     urinary frequency | |
|     sweating | |
|     giddiness, blurred vision | |
|     tinnitus | |
|     0 = Absent | |
|     1 = Mild | |
|     2 = Moderate | |
|     3 = Severe | |
|     4 = Incapacitating | ____ |
| Somatic symptoms: general | |
|     0 = None | |
|     1 = Heaviness in limbs, back or head; backaches, headaches, muscle aches, loss of energy, fatigability | |
|     2 = Any clear-cut symptom rates 2 | ____ |
| General Symptoms | |
| Symptoms such as: loss of libido, menstrual disturbances | |
|     0 = Absent | |
|     1 = Mild | |
|     2 = Severe | ____ |
| Hypochondriasis | |
|     0 = Not present | |
|     1 = Self-absorption (bodily) | |
|     2 = Preoccupation with health | |
|     3 = Strong conviction of some bodily illness | |
|     4 = Hypochondrial delusions | ____ |
| Loss of Weight | |
| Rate either 'A' or 'B': | |
| A When rating by history: | |
|     0 = No weight loss | |
|     1 = Probable weight loss associated with present illness | |
|     2 = Definite (according to patient) weight loss | |
| B Actual weight changes (weekly): | |
|     0 = Less than 1 lb (0.5 kg) weigh loss in one week | |
|     1 = 1-2 lb (0.5 kg-1.0 kg) weight loss in week | |
|     2 = Greater than 2 lb (1 kg) weight loss in week | |
|     3 = Not assessed | ____ |

TABLE 2a-continued

| Activity | Score |
|---|---|
| Insight | |
| 0 = Acknowledges being depressed and ill | |
| 1 = Acknowledges illness but attributes cause to bad food, overwork, virus, need for rest, etc. | |
| 2 = Denies being ill at all | |
| TOTAL SCORE: | |

The Fatigue Impact Scale (FIS). The Fatigue Impact Scale was designed as a fatigue-specific measure for patients in the in primary care setting and also as a research tool (Fisk J D, et al. Clin Infect Dis. 1994; 18:S79-83). It can be used as a clinical measure to guide intervention or treatment, and to assess change over time. FIS consists of 40 questions within these three groups: cognitive, physical, and psychosocial functioning. The person who is taking the test rates the extent to which fatigue causes problems in his/her life. The Fatigue Impact Scale (FIS) is one of the most widely used tools, although there now exist modified versions [the modified Fatigue Impact Scale (MFIS), the daily FIS, the unidimentional FIS and the abbreviated MFIS]. An example of a work sheet for calculation of the FIS is shown in table 2b below:

TABLE 2b

| Because of my fatigue: | 0—No Problem | 1—Small Problem | 2—Moderate Problem | 3—Big problem | 4—Extreme Problem |
|---|---|---|---|---|---|
| 1 I feel less alert | | | | | |
| 2 I feel that I am more isolated from social contact | | | | | |
| 3 I have to reduce my workload or responsibilities | | | | | |
| 4 I am more moody | | | | | |
| 5 I have difficulty paying attention for a long period of time | | | | | |
| 6 I feel I cannot think clearly | | | | | |
| 7 I work less effectively (this applies to work inside or outside the home) | | | | | |
| 8 I have to rely more on others to help me or do things for me | | | | | |
| 9 I have difficulty planning activities ahead of time because my fatigue may interfere with them | | | | | |
| 10 I am more clumsy and uncoordinated | | | | | |
| 11 I find I am more forgetful | | | | | |
| 12 I am more irritable and more easily angered | | | | | |
| 13 I have to be careful about pacing my physical | | | | | |
| 14 I am less motivated to do anything that requires | | | | | |
| 15 I am less motivated to engage in social activities | | | | | |
| 16 Fatigue limits my ability to travel outside my home | | | | | |
| 17 I have trouble maintaining physical effort for long | | | | | |
| 18 I find it difficult to make decisions | | | | | |
| 19 I have few social contact outside of my own home | | | | | |
| 20 Normal day-to-day events are stressful for me | | | | | |
| 21 I am less motivated to do anything that requires | | | | | |
| 22 I avoid situations that are stressful for me | | | | | |
| 23 My muscles feel much weaker than they should | | | | | |
| 24 My physical discomfort is increased | | | | | |
| 25 I have difficulty dealing with anything new | | | | | |

TABLE 2b-continued

| Because of my fatigue: | 0—No Problem | 1—Small Problem | 2—Moderate Problem | 3—Big problem | 4—Extreme Problem |
|---|---|---|---|---|---|
| 26 I am less able to finish tasks that require thinking | | | | | |
| 27 I feel unable to meet the | | | | | |
| 28 I am less able to provide financial support for myself | | | | | |
| 29 I engage in less sexual activity | | | | | |
| 30 I find it difficult to organize my thoughts when I am | | | | | |
| 31 I am less able to complete tasks that requires physical | | | | | |
| 32 I worry about how I look to other people | | | | | |
| 33 I am less able to deal with emotional issues | | | | | |
| 34 I feel slowed down in my thinking | | | | | |
| 35 I find it hard to concentrate | | | | | |
| 36 I have difficulty participating fully in family | | | | | |
| 37 I have to limit my physical activities | | | | | |
| 38 I require more frequent or longer periods of rest | | | | | |
| 39 I am not able to provide as much emotional support to | | | | | |
| 40 Minor difficulties seem like major difficulties | | | | | |

Pruritus score. The presence of pruritus and its score can be assessed in compliance with Hermine O, et al., PLoS ONE. 2008; 3:e2266 by means of the amended score rating shown in table 2c below (the pruritus score being the total of scores):

TABLE 2c

| ITEM | DEFINITION | GRADE | SCORE |
|---|---|---|---|
| Frequency of pruritus: | Every day | 1 | 3 |
| Pruritus is present | Every second day | 2 | 2 |
| | Sporadically | 3 | 1 |
| Intensity of pruritus | Disabling | 1 | 4 |
| | Significant | 2 | 3 |
| | Moderate | 3 | 2 |
| | Mild | 4 | 1 |
| Localization | Head | 1 | 0.5 |
| | Back | 2 | 0.5 |
| | Anterior surface of the trunk | 3 | 0.5 |
| | One hand | 4 | 0.5 |
| | Both hands | 5 | 1.0 |
| | One leg | 6 | 0.5 |
| | Both legs | 7 | 1.0 |
| Influence on well-being | Enormous | 1 | 3 |
| | Moderate | 2 | 2 |
| | Little | 3 | 1 |

In a large-scale and comprehensive analysis of disability in mastocytosis patients by AFIRMM (Association Française pour les Initiatives de Recherche sur le Mastocyte et les Mastocytoses), it was shown that patient's measurable and perceived handicaps did not differ according to disease classification or the presence or absence of associated biomarkers, i.e. the c-Kit D816V mutation or an elevated serum tryptase level (Hermine O, et al., 2008, PLoS ONE. 3:e2266). Key findings from the AFIRMM study were that indolent SM, smoldering SM and CM are not distinct diseases but part of a continuous spectrum of mast cell-related dysfunctions, with the level of mast cell activation and the systemic release of mediators being of principal importance rather than their presence per se. Furthermore, for the purposes of treatment it was proposed that SM should be classified on one hand as either mast cell leukemia or aggressive mastocytosis that absolutely required a cytoreductive treatment, or on the other hand indolent mastocytosis, which can be further subcategorized and treated according to the severity of patient's mast cell mediator release associated handicap.

In one embodiment, mastocytosis is cutaneous (CM) or systemic mastocytosis (SM) as defined in the WHO consensus classification system for mastocytosis.

The expression "systemic form of mastocytosis" as used in the present application, encompasses a subpopulation of patients from the overall mastocytosis patient population. The term "systemic mastocytosis" in this invention is to be fully distinguished from the broader terms "mastocytosis" or even "mast cell activation disease", which encompasses a collection of disorders or syndromes characterized by the accumulation of pathological mast cells in potentially any or all organs and tissues and/or the aberrant release of variable subsets of mast cell mediators.

In one embodiment "systemic mastocytosis" corresponds to the mastocytosis subpopulations of indolent systemic mastocytosis and smoldering systemic mastocytosis, as defined according to the World Health Organization (WHO) diagnostic criteria [Arock M, et al. Eur J Haematol. 2015 June; 94(6):474-90]. A diagnosis of systemic mastocytosis is made according to the presence of B-('Borderline Benign') findings and C-('Consider Cytoreduction') findings, which reflect the disease burden (B) and disease aggressiveness (C), respectively. Patients who have systemic mastocytosis without B- or C-findings and without signs of an associated clonal hematologic non-mast cell lineage disease (AHNMD) are diagnosed as "indolent systemic mastocytosis" (ISM). Patients who have two or more B-findings, but no C-findings, are diagnosed with "smoldering systemic mastocytosis" (SSM), a separate systemic mastocytosis category initially considered a subtype of ISM defined by a huge mass of neoplastic mast cells.

In another embodiment "systemic mastocytosis" is defined by the ABSSM diagnostic criteria, and thus relates to a disease for which any of the following four criteria are fulfilled at baseline or before baseline:

presence of mast cells in any bone marrow biopsy or aspirate associated with at least one sign of abnormality, wherein said abnormal signs are selected from the list comprising: more than 1% infiltration of mast cells in bone marrow; aggregates of more than 15 mast cells in bone marrow that can be described by the following words: nodules, seats, clusters, foci, or granuloma; more than 25% atypical mast cells in a sample of bone marrow; abnormal mast cells in the sample of bone marrow with microscopic testing that can be described by the following words: spindled, abnormal, atypical, fusiform, dystrophic, pathologic, dysmorphic; abnormal immunohistochemistry signs: mast cells in bone marrow express CD2 or/and CD25 present; and c-Kit point mutation at codon 816 (c-Kit 816) in bone marrow; or detection of c-Kit 816 in bone marrow without evidence of mast cells in bone marrow and detection of c-Kit 816 in skin biopsy justifying clonality; or presence of mast cells in bone marrow biopsy or aspirate without signs of mast cell abnormality; or excess of mast cells detected in digestive organs in addition to excess of mast cells in the skin.

In another embodiment "systemic mastocytosis" is defined by the Protocol AB06006 version 7.0 (v7) diagnostic criteria, and thus relates to a disease for which the following criteria are fulfilled:

patient with one of the following documented mastocytosis as per WHO classification: smoldering systemic mastocytosis or indolent systemic mastocytosis; and/or patient with documented mastocytosis and evaluable disease based upon histological criteria including typical infiltrates of mast cells in a multifocal or diffuse pattern in skin and/or bone marrow biopsy.

In one embodiment, mastocytosis is an indolent form of mastocytosis, as defined above based on WHO consensus classification system. In this embodiment, it is preferred to use a tyrosine kinase inhibitor or a mast cell inhibitor according to the invention not in combination with at least one cytoreductive or disease modifying drug, as defined below.

In one embodiment, mastocytosis is indolent systemic mastocytosis.

In another embodiment, mastocytosis is smoldering systemic mastocytosis.

In one embodiment, mastocytosis is an aggressive form of mastocytosis as defined above based on WHO consensus classification system. In this embodiment, it is preferred to use a tyrosine kinase inhibitor or a mast cell inhibitor according to the invention in combination with at least one cytoreductive or disease modifying drug, as defined below.

In one embodiment, severe systemic mastocytosis in a human patient is defined by the presence of severe mast cell mediator release associated handicap(s) in said human patient.

In other words, a human patient suffering from severe systemic mastocytosis is a human patient suffering from systemic mastocytosis with severe handicap(s) associated with mast cell mediator release.

In one embodiment, the subject is not a MCAS patient.

As disclosed above, the expression "mast cell activation syndrome" (MCAS), as used in the present application, encompasses a collection of clinical signs and symptoms resulting from the inappropriate activation of mast cells, wherein no proliferation or otherwise accumulation of mast cells is observed. According to an embodiment, MCAS corresponds to the syndrome defined by the Molderings criteria, or the Valent diagnostic criteria, or the Akin diagnostic criteria, as defined below.

In a first embodiment, MCAS is defined according to Molderings et al. (Molderings et al., Journal of Hematology & Oncology, 2011, 4:10), and thus relates to a syndrome for which both hereinafter major criteria or the second hereinafter major criterion and at least one hereinafter minor criterion are fulfilled:

Major Criteria:
  Multifocal or disseminated dense infiltrates of mast cells in bone marrow biopsies and/or in sections of other extracuteanous organ(s), e.g. gastrointestinal tract biopsies; CD117-, tryptase- and CD25-stained;
  Unique constellation of clinical complaints as a result of a pathologically increased mast cell activity (mast cell mediator release syndrome).

Minor Criteria:
  Mast cells in bone marrow or other extracuteanous organ(s) show an abnormal morphology (>25%) in bone marrow smears or in histologies;
  Mast cells in bone marrow express CD2 and/or CD25;
  Detection of genetic changes in mast cells from blood, bone marrow or extracuteanous organs for which an impact on the state of activity of affected mast cells in terms of an increased activity has been proved;
  Evidence of a pathologically increased release of mast cell mediators by determination of the content of: tryptase in blood, N-methylhistamine in urine, heparin in blood, chromogranin A in blood, other mast cell-specific mediators (e.g. leukotrienes, prostaglandin $D_2$).

In a second embodiment, the term MCAS is defined by the Valent diagnostic criteria (Valent et al, Int Arch Allergy Immunol 2012, 157:215-225), and thus relates to a syndrome for which the following criteria are fulfilled:
  1. typical clinical signs and symptoms, including: flushing, pruritus, urticaria, angioedema, nasal congestion, nasal pruritus, wheezing, throat swelling, headache, hypotension, and diarrhea.
  2. Substantial and transient increase in an mast cell (MC)-derived mediator in biological fluids [preferably serum total tryptase, but also histamine/histamine metabolites and prostaglandin D2 (PGD2)/PGD2 urinary metabolites] during or shortly after the acute event compared to a baseline level recorded either before the acute event or at least 24 h after all clinical signs and symptoms of the event have completely resolved.
  3. An objective major response of clinical symptoms to agents that attenuate the production or activity of MC-derived mediators.

According to the definition of Valent et al, all three criteria should be met to define MCAS. However, in some circumstances, a patient may not respond to a drug and may even require intensive care and epinephrine administration. In such a patient, the condition may still be considered as MCAS if typical symptoms (1) and an increase in MC mediators (2) are present, and a primary underlying MC disease (e.g. SM) or an underlying IgE-mediated disease (e.g. allergy) is known.

In a third embodiment, the term MCAS is defined by the Akin diagnostic criteria (Akin et al, J Allergy Clin Immunol, 2010, 126(6):1099-1104), and thus relates to a syndrome for which the following criteria are fulfilled:
- Episodic symptoms consistent with mast cell mediator release affecting two or more organ systems evidenced as follows:
  - skin: urticarial, angioedema, flushing;
  - gastrointestinal: nausea, vomiting, diarrhea, abdominal cramping;
  - cardiovascular: hypotensive syncope or near syncope, tachycardia;
  - respiratory: wheezing;
  - naso-ocular: conjunctival injection, pruritus, nasal stuffiness;
- A decrease in the frequency or severity, or resolution of symptoms with anti-mediator therapy: H1 and H2 histamine receptor antagonists, anti-leukotriene medications (cysLT receptor blockers or 5-LO inhibitor), or mast cell stabilizers (cromolyn sodium);
- Evidence of an elevation in a validated urinary or serum marker of mast cell activation: documentation of elevation of the marker above the patient's baseline during a symptomatic period on at least two occasions; or if baseline tryptase levels are persistently >15 ng, documentation of elevation of the tryptase above baseline in one occasion. Total serum tryptase is recommended as the markers of choice; less specific (also from basophils) 24 hours urine histamine metabolites or 11-beta-prostaglandin F2;
- Primary (clonal) and secondary disorders of mast cell activation ruled out. Primary disorders of mast cell activation include: anaphylaxis with an associated clonal mast cell disorder, and monoclonal mast cell activation syndrome (MMAS). Secondary disorders of mast cell activation include: allergic disorders, mast cell activation associated with chronic inflammatory or neoplastic disorders, physical urticarias, chronic autoimmune urticaria.

Tyrosine Kinase Inhibitors (Compounds of the invention)

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation. A tyrosine kinase inhibitor is a drug that inhibits tyrosine kinases, thereby interfering with signaling processes within cells. Blocking such processes can stop the cell growing and dividing.

In one embodiment, the tyrosine kinase inhibitor of the invention has the following formula [A]:

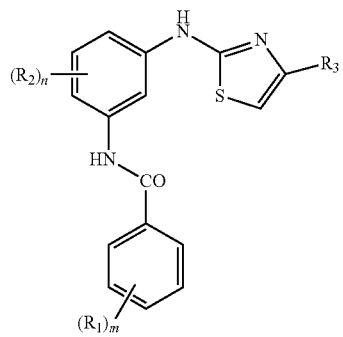

[A]

wherein $R_1$ and $R_2$, are selected independently from hydrogen, halogen, a linear or branched alkyl, cycloalkyl group containing from 1 to 10 carbon atoms, trifluoromethyl, alkoxy, cyano, dialkylamino, and a solubilising group, m is 0-5 and n is 0-4;

the group $R_3$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, cyano and alkoxy;
(ii) a heteroaryl group such as 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

or a pharmaceutically acceptable salt or solvate thereof.

Tyrosine kinase inhibitors of formula [A] can preferably be used as c-Kit inhibitors.

Unless otherwise specified, the below terms used herein are defined as follows:

As used herein, the term an "aryl group" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents. In one embodiment, the aryl group is a monocyclic ring, wherein the ring comprises 6 carbon atoms, referred to herein as "$(C_6)$aryl".

As used herein, the term "alkyl group" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo [1,2-a]pyridyl, and benzo(b)thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

The term "heterocycle" as used herein, refers collectively to heterocycloalkyl groups and heteroaryl groups.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —C(O) $NR_{11}R_{12}$, —$NR_{13}C(O)R_{14}$, a halo, —$OR_B$, cyano, nitro, a haloalkoxy, —$C(O)R_{13}$, —$NR_{11}R_{12}$, —$SR_{13}$, —$C(O)OR_{13}$, —$OC(O)R_{13}$, —$NR_{13}C(O)NR_{11}R_{12}$, —$OC(O)NR_{11}R_{12}$, —$NR_{13}C(O)OR_{14}$, —$S(O)rR_{13}$, —$NR_{13}S(O)rR_{14}$, —$OS(O)rR_{14}$, $S(O)rNR_{11}R_{12}$, —O, —S, and —N—$R_{13}$, wherein r is 1 or 2; $R_{11}$ and $R_{12}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or $R_{11}$ and $R_{12}$ taken together with the nitrogen to which they are attached is optionally substituted heterocycloalkyl or optionally substituted heteroaryl; and $R_{13}$ and $R_{14}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl. In certain embodiments, the term "substituent" or the adjective "substituted" refers to a solubilising group.

The term "solubilising group" means any group which can be substantially ionized and that enables the compound to be soluble in a desired solvent, such as, for example, water or water-containing solvent. Furthermore, the solubilising group can be one that increases the compound or complex's lipophilicity. Typically, the solubilising group is selected from alkyl group substituted with one or more heteroatoms such as N, O, S, each optionally substituted with alkyl group substituted independently with alkoxy, amino, alkylamino, dialkylamino, carboxyl, cyano, or substituted with cycloheteroalkyl or heteroaryl, or a phosphate, or a sulfate, or a carboxylic acid. For example, by "solubilising group" it is referred herein to one of the following:

- an alkyl, cycloalkyl, aryl, heretoaryl group comprising either at least one nitrogen or oxygen heteroatom or which group is substituted by at least one amino group or oxo group
- an amino group which may be a saturated cyclic amino group which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl
- one of the structures a) to i) shown below, wherein the wavy line and the arrow line correspond to the point of attachment to core structure of formula I

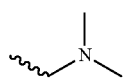

a

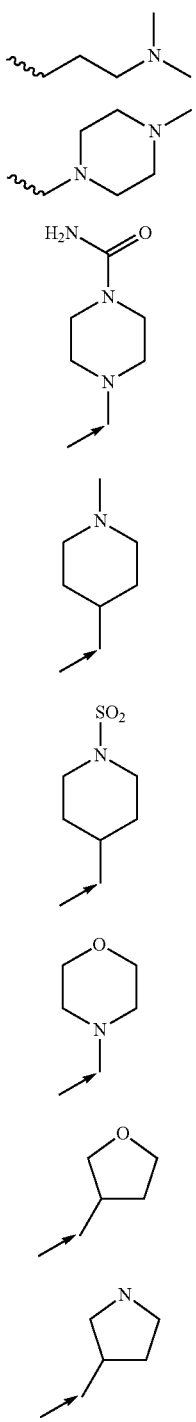

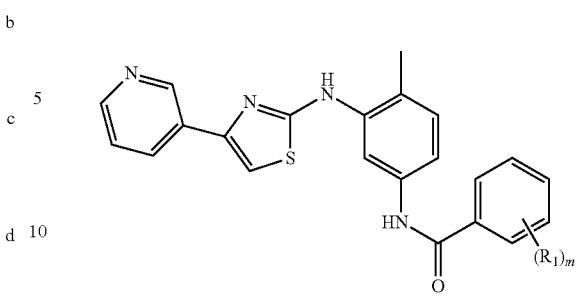

wherein:

R₁ is selected independently from hydrogen, halogen, a linear or branched alkyl, cycloalkyl group containing from 1 to 10 carbon atoms, trifluoromethyl, alkoxy, amino, alkylamino, dialkylamino, solubilising group, and m is 0-5, or a pharmaceutically acceptable salt or solvate thereof.

The term "pharmaceutically acceptable salt, solvate, carrier or excipient" refers to a salt, solvate, excipient or carrier that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, injected preparations should meet sterility, pyrogenicity, general safety and purity standards as required by regulatory offices, such as, for example, FDA Office or EMA.

The term "solvate" is used herein to describe a molecular complex comprising the compound of the invention and one or more pharmaceutically acceptable solvent molecules, for example, ethanol.

Pharmaceutically acceptable salts preferably are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic, in particular methanesulfonic acid, or aromatic sulfonic acids, for example benzene-, p-toluene- or naphthalene-2-sulfonic acid.

Unless otherwise indicated, references to "mesilate" are used in the present invention to refer to a salt of methanesulfonic acid with a named pharmaceutical substance (such as compounds of formula [A] or [B]). Use of mesilate rather than mesylate is in compliance with the INNM (International nonproprietary names modified) issued by WHO (e.g. *World Health Organization (February* 2006). *International Nonproprietary Names Modified*. INN Working Document 05.167/3. WHO.). For example, masitinib or imatinib mesilate mean the methanesulfonic acid salt of masitinib and imatinib, respectively.

The term "cycloalkyl" means a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

The term "halogen" means —F, —Cl, —Br or —I.

In a particular embodiment the tyrosine kinase inhibitor of the invention has general formula [B], Masitinib is a Potent c-Kit kinase and Mast Cell Inhibitor In one highly preferred embodiment, the tyrosine kinase inhibitor of formula [B] is masitinib or a pharmaceutically acceptable salt or solvate thereof, more preferably masitnib mesilate.

Preferably, "masitnib mesilate" means the orally bioavailable mesylate salt of masitinib—CAS 1048007-93-7 (MsOH); C28H30N6OS.CH3SO3H; MW 594.76:

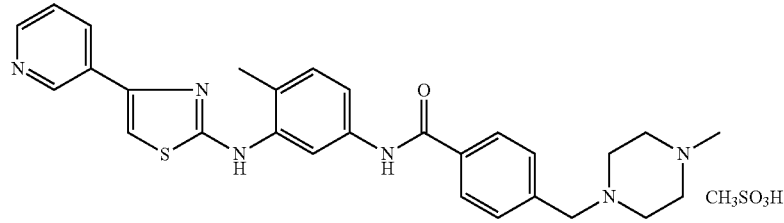

New potent and selective c-kit inhibitors are 2-(3-aminoaryl)amino-4-aryl-thiazoles described in AB Science's PCT application WO 2004/014903.

Masitinib is a small molecule selectively inhibiting specific tyrosine kinases such as c-Kit, PDGFR, Lyn, Fyn and to a lesser extent the fibroblast growth factor receptor 3 (FGFR3), without inhibiting, at therapeutic doses, kinases associated with known toxicities (i.e. those tyrosine kinases or tyrosine kinase receptors attributed to possible tyrosine kinase inhibitor cardiac toxicity, including ABL, KDR and Src) (Dubreuil et al., 2009, PLoS ONE 2009. 4(9):e7258). The chemical name for masitinib is 4-(4-methylpiperazin-1-ylmethyl)-N-[4-methyl-3-(4-pyridin-3ylthiazol-2-ylamino)phenyl]benzamide—CAS number 790299-79-5.

Masitinib was described in U.S. Pat. No. 7,423,055 and EP1525200B1. A detailed procedure for the synthesis of masitinib mesilate is given in WO2008/098949.

Masitinib's strong inhibitory effect on wild-type and juxtamembrane-mutated c-Kit receptors, results in cell cycle arrest and apoptosis of cell lines dependent on c-Kit signaling (Dubreuil et al., 2009, PLoS ONE, 4(9):e7258). Stem cell factor, the ligand of the c-Kit receptor, is a critical growth factor for mast cells; thus, masitinib is an effective antimastocyte, exerting a direct antiproliferative and pro-apoptotic action on mast cells through its inhibition of c-Kit signaling. Moreover, in vitro, masitinib demonstrated greater activity and selectivity against c-Kit than imatinib, inhibiting recombinant human wild-type c-Kit with an half inhibitory concentration ($IC_{50}$) of 200±40 nM and blocking stem cell factor-induced proliferation and c-Kit tyrosine phosphorylation with an $IC_{50}$ of 150±80 nM in Ba/F3 cells expressing human or mouse wild-type c-Kit. In contrast, masitinib only weakly inhibited the proliferation of Ba/F3 cells expressing the D816V c-Kit mutation with an $IC_{50}$ of 5.0±2.0 µM.

In addition to its antiproliferative properties, masitinib can also regulate the activation of mast cells through its targeting of Lyn and Fyn, key components of the transduction pathway leading to IgE induced degranulation (Gilfillan & Tkaczyk, 2006, Nat Rev Immunol, 6:218-230; Gilfillan et al., 2009, Immunological Reviews, 228:149-169). This can be observed in the inhibition of FcεRI-mediated degranulation of human cord blood mast cells (Dubreuil et al., 2009, PLoS ONE; 4(9):e7258). Moreover, it has been shown that Lyn is an important signaling molecule that contributes to growth of neoplastic mast cells in advanced systemic mastocytosis [Gleixner et al. Blood. 2011 Aug. 18; 118(7):1885-98].

Treatment of Mastocytosis with Masitinib

Molecules able to inhibit the survival and/or activation of mast cells may be able to control the symptoms and progression of mastocytosis or any related disease. In connection with the present invention, we consider that a tyrosine kinase inhibitor or a mast cell inhibitor, notably as defined above, especially masitinib, through its inhibition of mast cell proliferation and activation, is fulfilling this role in the treatment of mastocytosis via, but not limited to, reducing the overall mast cell burden and inhibiting the global activity of mast cells. This is achieved despite masitinib not directly inducing apoptosis in mast cells with the D816V c-Kit mutation. Wild-type c-Kit mast cells contribute to the widespread inflammatory cascade orchestrated by the constitutive activation of the D816V c-Kit mutated mast cells, effectively amplifying their influence. Thus, lowering the overall mast cell burden via depletion of wild-type c-Kit mast cells lessens the symptoms of mastocytosis patients by 'containing' or 'isolating' the problematic mutated mast cells and thereby, dampening their effect.

In connection with the present invention, it would seem, without wishing to be bound by a theory, that surprisingly a tyrosine kinase inhibitor or a mast cell inhibitor, notably as defined above, especially masitinib could also be of further therapeutic benefit against mastocytosis by inhibiting mast cell degranulation or activity via inhibition of Lyn and Fyn. This is highly significant as it represents a mechanism of action that is independent from the c-Kit signaling pathway or survival of mast cells, i.e. will affect equally mast cells with both wild-type c-Kit and mutated D816V c-Kit. It follows that the subsequent decrease in mast cell degranulation or activity would lead to a lessening of mast cell mediator release symptoms and mastocytosis related handicap. In addition, a reduction in release of various chemoattractants associated with mast cell migration will lessen the rate of mast recruitment and accumulation, further 'isolating' the mutated cells. For example, SCF is a chemotactic factor for mast cells with the activating D816V c-Kit mutation showing enhanced cell migration towards the SCF source; moreover, mast cells themselves possess the capacity to synthesize, store and release SCF. Thus, expression of SCF is increased in the constitutive activation of D816V c-Kit mutated mast cells, with subsequent migration of other mast cells, and preferentially D816V c-Kit mutated mast cells, towards this source of SCF, cumulating in mast cell accumulation. If the constitutive mast cell mediator release encountered in mastocytosis is due to an intrinsic defect, i.e. mutation, lowering of the activation threshold of mast cells, then masitinib's inhibition of degranulation or activity would help compensate or restore normal function, with respect to mediator hypersecretion and release of the mast cell chemoattractants, such as SCF.

Thus, a tyrosine kinase inhibitor or a mast cell inhibitor, notably as defined above, especially masitinib's anti mast cell properties appear particularly well adapted to the treatment of mastocytosis with mast cell mediator release associated handicap, and in particular indolent forms of mastocytosis; a reduction of mast cell activity via the inhibitory action of masitinib on c-Kit, Lyn and Fyn tyrosine kinase activity, impacting both the overall mast cell burden and inflammatory cascade as well as the threshold of mast cell degranulation or activation and migration/recruitment of mast cells. Unexpectedly, without wishing to be bound by a theory, it is through this multifaceted mechanism of action that a compound of the invention can elicit a response in patients of both positive and negative D816V c-Kit mutation status.

Considering the synergistic effects of masitinib on different pathways involved in mast cells mediator release, we investigated the efficacy and safety of oral masitinib in a subpopulation of mastocytosis patients diagnosed with indolent forms of mastocytosis and showing associated handicap. We also further tested if this clinically relevant dose regimen could benefit to both D816V positive and D816V negative mastocytosis patients. Evidence that masitinib is a viable therapeutic strategy for indolent mastocytosis, capable of reducing symptoms and severity of mast cell mediator release associated handicap in patients with positive and negative D816V c-Kit mutation status, was reported by two phase 2 studies. The first of these clinical trials reported similar efficacy patterns in response to treatment with masitinib regardless of a patient's c-Kit status. A second phase 2 study with a positive D816V c-Kit mutation cohort confirmed that masitinib was indeed significantly effective in reducing this population's level of mast cell mediator release associated handicap, with response rates being consistent with those previously observed. That is to say, masitinib proved to be of therapeutic benefit to both D816V positive and D816V negative mastocytosis patients.

Thus, in a first embodiment, the invention relates to the use of at least one compound of the invention (i.e. a tyrosine kinase inhibitor or a mast cell inhibitor, especially masitinib or a pharmaceutically acceptable salt or solvate thereof), for the preparation of a medicament for the treatment of mastocytosis, and in particular cutaneous or systemic mastocytosis, in human patients, wherein said tyrosine kinase inhibitor or mast cell inhibitor is to be administered to patients in need thereof, optionally combined with at least one other cytoreductive or disease modifying drug, and wherein said patients optionally suffer from mast cell mediator release associated handicap with an overall patient assessment (OPA) ≥1.

The invention thus relates to a method of treatment of mastocytosis, and in particular cutaneous or systemic mastocytosis, in human patients, wherein at least one compound of the invention is to be administered in patients in need thereof, optionally combined with at least one other cytoreductive or disease modifying drug, and wherein said patients optionally suffer from mast cell mediator release handicap with an overall patient assessment (OPA) ≥1.

Preferably, said patients are those afflicted by mastocytosis with mast cell mediator release associated handicap of mild disability to those with intolerable disability; more specifically with OPA scores of between: 1 to 4 (mild disability to intolerable disability), or 2 to 4 (moderate disability to intolerable disability), or even 3 to 4 (severe disability to intolerable disability).

In one embodiment, said patients' mast cell mediator release associated handicap is defined as presenting with at least two mast cell mediator release associated handicaps selected from the group consisting of pruritus, flushes, depression, diarrhea, pollakiuria (also referred to as micturition frequency syndrome), and asthenia; wherein at least one handicap is selected from the group consisting of pruritus, flushes, depression, and asthenia, and preferably wherein if present handicaps have the following scores: pruritus score ≥6, number of flushes per week ≥7; depression: Hamilton rating scale score ≥10, diarrhea: number of stools per day ≥4; pollakiuria: number of micturitions per day ≥8; asthenia: Fatigue Impact Scale total score ≥40.

In another embodiment, said patients' mast cell mediator release associated handicap is defined as presenting with at least two mast cell mediator release associated handicaps selected from the group consisting of pruritus, flushes, depression, diarrhea, pollakiuria (also referred to as micturition frequency syndrome), and asthenia; wherein at least one handicap is selected from the group consisting of pruritus, flushes, depression, and asthenia, and preferably wherein if present handicaps have the following scores: pruritus score ≥6; number of flushes per week ≥7; depression: Hamilton rating scale score ≥14; diarrhea: number of stools per day ≥4; pollakiuria: number of micturitions per day ≥8; asthenia: Fatigue Impact Scale total score ≥75.

In another embodiment, said patients' mast cell mediator release associated handicap is defined as presenting with at least one (i.e. 1, 2, 3, or 4) severe mast cell mediator release associated handicaps selected from the group consisting of pruritus score ≥9; number of flushes per week ≥8; depression measured by the Hamilton rating scale ≥19 and asthenia (fatigue) with a fatigue score measured by Fatigue Impact Scale (FIS) ≥75 (or any equivalent cut-off determined using the FSS, FSI, BFI or MAF).

In one embodiment the present invention relates to a method for treating severe systemic mastocytosis in human patients comprising administering a tyrosine kinase inhibitor or a pharmaceutically acceptable salt or solvate thereof, wherein said severe mastocytosis is associated with at least two of the six following mast cell mediator release associated handicaps: a pruritus score ≥9; a number of flushes per week ≥8; a Hamilton rating scale for depression (HAMD-17) score ≥19; a number of stools per day ≥4; a number of micturition per day ≥8; a fatigue score (asthenia) measured by Fatigue Impact Scale ≥75, wherein at least one handicap is selected among pruritus, flushes, depression and fatigue. (asthenia).

In one embodiment, individual handicaps and corresponding scores are defined and calculated as disclosed above.

According to an embodiment, said compound of the invention is to be administered for the treatment of cutaneous mastocytosis, and in particular cutaneous mastocytosis with mast cell mediator release associated handicap.

According to another embodiment, said compound of the invention is to be administered for the treatment of systemic mastocytosis (such as, for example, indolent systemic mastocytosis or smoldering systemic mastocytosis), and in particular systemic mastocytosis with mast cell mediator release associated handicap.

According to another embodiment, said compound of the invention is to be administered for the treatment of severe systemic mastocytosis, and in particular severe systemic mastocytosis with at least one mast cell mediator release associated handicap selected from pruritus score ≥9; number of flushes per week ≥8; depression measured by the Hamilton rating scale ≥19 and asthenia (fatigue) with a fatigue score measured by Fatigue Impact Scale (FIS) ≥75 (or any equivalent cut-off determined using the FSS, FSI, BFI or MAF.

A preferred salt of masitinib is masitinib mesilate.

According to one embodiment, a compound of the invention, is an inhibitor of wild-type c-Kit and/or Lyn or Fyn kinase activity but inactive against the D816V mutation of c-Kit, and wherein said mastocytosis patients are classified as either c-Kit D816V positive or c-Kit D816V negative.

According to another embodiment, a compound of the invention is to be administered at a starting daily dose of 3.0 to 6.0 mg/kg/day, with the preferred embodiment for patients with indolent mastocytosis with mast cell mediator release associated handicap being a starting daily dose of 4.5 to 6.0 mg/kg/day.

According to another embodiment, a compound of the invention, preferably masitinib or a pharmaceutically acceptable salt or solvate thereof, more preferably masitinib mesilate is to be administered at a dose of 1.5, 3.0, 4.5, 6.0, 7.5, or 9.0 mg/kg/day (mg per kilo body weight per day).

Preferably, a compound of the invention is dose escalated by increments of 1.5 mg/kg/day to reach a maximum of 9.0 mg/kg/day.

According to another embodiment, a compound of the invention, preferably masitinib or a pharmaceutically acceptable salt or solvate thereof, more preferably masitinib mesilate is to be initially administered at a dose of 3.0 mg/kg/day during at least 4 weeks, then 4.5 mg/kg/day during at least 4 weeks, and at 6 mg/kg/day thereafter, with each dose escalation being subjected to toxicity controls.

According to an embodiment, patients are those afflicted with mastocytosis with mast cell mediator release associated handicap, and in particular cutaneous or systemic mastocytosis, wherein said patients have a positive D816V c-Kit mutation status.

According to another embodiment, patients are those afflicted with mastocytosis with mast cell mediator release associated handicap, and in particular cutaneous or systemic mastocytosis, wherein said patients have a negative D816V c-Kit mutation status.

According to another embodiment, patients are those afflicted with mastocytosis with mast cell mediator release associated handicap, and in particular cutaneous or systemic mastocytosis, wherein said patients have a mixed c-Kit mutation status defined as both positive and negative D816V c-Kit mutation status with mast cell infiltrated organs.

Said compound of the invention is preferably administered orally.

Said compound of the invention is preferably administered twice a day.

Advantageously, the use or method comprises a long-term administration of an effective amount of said tyrosine kinase inhibitor or mast cell inhibitor, especially masitinib or a pharmaceutically acceptable salt or solvate thereof, over more than 3 months, preferably more than 12 months.

According to one embodiment, a compound of the invention, preferably masitinib or a pharmaceutically acceptable salt or solvate thereof, more preferably masitinib mesilate is comprised in a pharmaceutical composition in an amount of at least 50 mg and less than 600 mg, preferably of at least 100 mg and less than 400 mg.

For example, said pharmaceutical composition comprises a dose of at least 50 mg and less than 150 mg, and preferably of 100 mg, of said compound(s) of the invention. For example, said pharmaceutical composition comprises a dose of at least 150 mg and less than 400 mg, and preferably of 200 mg, of said compound(s) of the invention.

According to a preferred embodiment, the compound of the invention is administered for the treatment of indolent mastocytosis with mast cell mediator release associated handicap, and in particular cutaneous or systemic mastocytosis, in combination with at least one other cytoreductive or disease modifying drug.

According to a preferred embodiment, the compound of the invention is administered for the treatment of aggressive forms of mastocytosis with mast cell mediator release associated handicap, and in particular Systemic Mastocytosis with an Associated clonal Hematologic Non Mast cell lineage Disease, Aggressive Systemic Mastocytosis, Mast Cell Leukemia, Mast Cell Sarcoma, or Extracutaneous Mastocytoma, in combination with at least one other cytoreductive or disease modifying drug.

The second cytoreductive or disease modifying drug is preferably selected from the group consisting of interferon-alpha (IFN-α), cladribine (2-CdA), hydroxyurea, a c-Kit kinase inhibitor, including imatinib, dasatinib or midostaurin (PKC412), and any combination of these cytoreductive or disease modifying drugs.

The compound(s) of the invention and one or more cytoreductive or disease modifying drugs may be to be administered separately, simultaneously or sequentially in time.

The invention also relates to a tyrosine kinase inhibitor or a mast cell inhibitor, notably as defined above, especially masitinib for use as a medicament or in a pharmaceutical composition for a method as defined in the description.

In another embodiment, the invention also relates to a method of treatment of mastocytosis, and in particular indolent forms of mastocytosis, in human patients, wherein a tyrosine kinase inhibitor or a mast cell inhibitor, especially masitinib or a pharmaceutically acceptable salt or solvate thereof, is administered for the treatment of mastocytosis with mast cell mediator release associated handicap in combination with at least one other cytoreductive drug; for example, interferon-alpha (IFN-α), cladribine (2-CdA), hydroxyurea, and c-Kit kinase inhibitors including imatinib, dasatinib or midostaurin (PKC412).

In one embodiment, said tyrosine kinase inhibitor or mast cell inhibitor, especially masitinib or a pharmaceutically acceptable salt or solvate thereof, is administered for the treatment of mastocytosis with mast cell mediator release associated handicap, and in particular indolent forms of mastocytosis, wherein said patients have a negative D816V c-Kit mutation status.

In another embodiment, said tyrosine kinase inhibitor or mast cell inhibitor, especially masitinib or a pharmaceutically acceptable salt or solvate thereof, is administered for the treatment of mastocytosis with mast cell mediator release associated handicap, and in particular indolent forms of mastocytosis, wherein said patients have a positive D816V c-Kit mutation status.

Advantageously, in the use or the method above, said patients have a mast cell mediator release associated handicap score of ≥1 on the overall patient assessment (OPA) scale for disability. Patients according to the invention are those afflicted with mastocytosis, and in particular indolent forms of mastocytosis, having mast cell mediator release associated handicap of mild severity to those with intolerable disability; more specifically with OPA scores of between: 1 to 4 (mild disability to intoleradble disability), or 2 to 4 (moderate disability to intolerable disability), or even 3 to 4 (severe disability to intolerable disability).

In one embodiment, the invention relates to the treatment of patients diagnosed as having mastocytosis with mast cell mediator release associated handicap, in particular indolent forms of mastocytosis with mast cell mediator release associated handicap, wherein handicapped status is as defined above.

Regarding best dosage regimen, said tyrosine kinase inhibitor or mast cell inhibitor, especially masitinib or a pharmaceutically acceptable salt or solvate thereof, is to be administered at a starting daily dose of 3.0 to 6.0 mg/kg/day; nonetheless said tyrosine kinase inhibitor or mast cell inhibitor, especially masitinib or a pharmaceutically acceptable salt or solvate thereof, can be dose escalated by increments of 1.5 mg/kg/day to reach a maximum of 9.0 mg/kg/day in low responder patients.

Indeed, depending on age, individual condition, mode of administration, and the clinical setting, effective doses of said tyrosine kinase inhibitor or mast cell inhibitor, especially masitinib or a pharmaceutically acceptable salt or solvate thereof, in human patients with mastocytosis with mast cell mediator release associated handicap are 3.0 to 6.0 mg/kg/day per os, preferably in two daily intakes. For adult human patients with indolent mastocytosis with mast cell mediator release associated handicap, a starting dose of said tyrosine kinase inhibitor or mast cell inhibitor, especially masitinib or a pharmaceutically acceptable salt or solvate thereof, of 4.5 to 6.0 mg/kg/day has been found to be the preferred embodiment according to the invention. For patients with an inadequate response after an assessment of response to therapy and in the absence of limiting toxicities, dose escalation of said tyrosine kinase inhibitor or mast cell inhibitor, especially masitinib or a pharmaceutically acceptable salt or solvate thereof, to a maximum of 9.0 mg/kg/day can be safely considered and patients may be treated as long as they benefit from treatment and in the absence of limiting toxicities.

Dose adjustment can be considered a dynamic process, with a patient undergoing multiple increases and/or decreases to optimize the balance between response and toxicity throughout treatment, both of which are likely to vary over time and duration of drug exposure. If dose escalation is undertaken, it is suggested that the starting dose of 3.0 to 6.0±1.5 mg/kg/day be incremented by 1 to 2 mg/kg/day up to a maximum dose of 9.0 mg/kg/day, over a period which depends upon clinical observations. For example, a single dose escalation of said tyrosine kinase inhibitor or mast cell inhibitor, especially masitinib or a pharmaceutically acceptable salt or solvate thereof, and preferably masitinib mesilate may take from 1 to 2 months. It is also contemplated herein that to fully obtain the therapeutic benefits of a patient-optimized dose of said tyrosine kinase inhibitor or mast cell inhibitor, especially masitinib or a pharmaceutically acceptable salt or solvate thereof, dose increments smaller than 1 to 2 mg/kg/day could be implemented. Dose reduction is to be considered to reduce toxicity in appropriate cases.

Any dose indicated herein refers to the amount of active ingredient as such, not to its salt or solvate form.

Given that the masitinib dose in mg/kg/day used in the described dose regimens refers to the amount of active ingredient masitinib, compositional variations of a pharmaceutically acceptable salt of masitinib mesilate will not change the said dose regimens.

Masitinib may be administered via different routes of administration but oral administration is preferred. Thus, in still another preferred embodiment, in the use or the method above, masitinib or salts thereof, is administered orally; preferably twice a day for long term period such as over more than 6 months, preferably more than 12 months. Masitinib can be administered in the form of 100 and 200 mg tablets.

According to a particular embodiment, the composition of the invention is an oral composition.

As is known to the person skilled in the art, various forms of excipients can be used adapted to the mode of administration and some of them can promote the effectiveness of the active molecule, e.g. by promoting a release profile rendering this active molecule overall more effective for the treatment desired.

The pharmaceutical compositions of the invention are thus able to be administered in various forms, more specially for example in an injectable, pulverizable or ingestible form, for example via the intramuscular, intravenous, subcutaneous, intradermal, oral, topical, rectal, vaginal, ophthalmic, nasal, transdermal or parenteral route. A preferred route is oral administration. The present invention notably covers the use of a compound according to the present invention for the manufacture of pharmaceutical composition.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Masitinib as a Chemosensitizer for Combination Therapies

In the present invention as defined above, the use or the method of treating mastocytosis with mast cell mediator release associated handicap, and in particular human patients with cutaneous or systemic mastocytosis, in particular as defined by WHO, with a tyrosine kinase inhibitor or a mast cell inhibitor, especially masitinib or a pharmaceutically acceptable salt or solvate thereof, can optionally be combined with at least one cytoreductive or disease modifying drug. The optional cytoreductive or disease modifying drug, dosed ideally in accordance to the manufacture's recommendations, could for example be, and without particular limitation, either: interferon-alpha (IFN-α), cladribine (2-CdA), hydroxyurea, imatinib, dasatinib or midostaurin (PKC412). In this regard, masitinib and at least one disease modifying drug are to be administered separately, simultaneously or sequentially in time.

There is in vitro and in vivo evidence that masitinib can modulate the activity of other drugs when administered in combination with said drug, for example, cytoreductive or disease modifying drugs. Such masitinib-induced chemosensitisation may allow for: (i) treatment of refractory patients via resensitizing of drug resistant cells; (ii) lowering the dose of standard treatment drugs, thereby reducing risk and tolerability; (iii) or increasing the available efficacy of standard treatment drugs at standard doses. In vivo and in vitro studies have shown that masitnib can enhance the antiproliferative effects of gemcitabine in human pancreatic cancer (Humbert M, et al. PLoS ONE. 2010; 5(3): e9430. doi:10.1371/journal.pone.0009430; Mitry, E. et al. Cancer Chemotherapy and Pharmacology. 2010; 66(2):395-403).

The present invention is illustrated by means of the following examples.

Example 1

Phase IIa, Open-Label, Randomized Study of Oral Masitinib in Patients with Systemic Indolent or Cutaneous Mastocytosis, with Mast Cell Mediator Release Associated Handicap and not Bearing Activating Point Mutations in the Phosphotransferase Domain of c-Kit Such as the Main Mutation Asp-816-Val (D816V)

Methods

Study Design

This was a phase 2a, multicentre, open-label trial over 12-weeks, with an extension phase possible for those patients experiencing improvement, to evaluate the dose response of masitinib in indolent forms of mastocytosis with handicap. Dose ranging was performed by randomly assigning patients (1:1 ratio) into initial treatment groups of 3 or 6 mg/kg/day. Masitinib, supplied as 100 and 200 mg tablets (AB Science, France), was administered orally in two daily intakes. Dose adjustments of 1.5 mg/kg/day were permitted, with the dosage being incremented in case of insufficient response accompanied by minimal toxicity (mild/moderate) at weeks 4 and 8. In the event of severe toxicity, masitinib was temporarily interrupted and then resumed at the same dosage upon recovery. If toxicity persisted, treatment was interrupted until the adverse event (AE) was resolved, followed by a reduction in masitinib dosage or treatment discontinuation.

Eligible patients were aged >18 years, had previously documented indolent systemic, smoldering systemic or cutaneous mastocytosis as per the WHO classification with associated disability as the result of mast cell released mediators and had not responded to usual symptomatic treatments for more the 6 months. Additionally, because masitinib exhibits a poor activity against D816V mutations, patients must have presented with at least one histologically proven infiltrated organ, (i.e. skin or bone marrow), in which the D816V mutation was absent or below the threshold of detection. A single occurrence of this criterion was deemed sufficient for inclusion and so no systematic examination of multiple organs was carried out specifically for this study. This mutation status did not constitute part of the patient's diagnosis but was rather a confirmatory test that the patient population could be better expected to show a response to treatment in this proof-of-concept study.

Patients were classified as having a handicap if after appropriate symptomatic treatments they fulfilled at least one of the following a priori criteria: number of flushes/day $\geq 1$; pruritus score $\geq 6$; number of stools $\geq 4$/day; micturition frequency $\geq 8$/day; Hamilton rating for depression $\geq 10$; or EORTC quality-of-life questionnaire (QLQ-C30) symptom score, functional score, and global health status of >0. Patients were excluded if they experienced inadequate organ function defined via blood test levels, or an Eastern Cooperative Oncology Group performance status >2. Other exclusion criteria included: life expectancy <6 months, severe or uncontrolled medical disease, and patients who were pregnant or nursing.

Response and Safety Assessment

In accordance to the AFIRMM study (Hermine O, et al., 2008, PLoS ONE. 3:e2266), evaluation of treatment response was based upon the change of clinical symptoms associated with a patient's handicaps at week 12 (W12) relative to baseline. Primary endpoints were daily frequency of flushes; pruritus score; and Hamilton rating for depression, as well as, daily stool and micturition frequencies; QLQ-C30 global health status, functional, and symptom scores. For each patient, all response parameters were recorded on the first day of treatment (baseline) prior to administration of masitinib and then again after 2, 4, 8 and 12 weeks of treatment. For those patients entering the extension phase, assessments were performed every 4 weeks for the first 3 months of extension, and every 12 weeks thereafter. Secondary endpoints included the W12 assessment of AFIRMM score (a validated questionnaire assessing the self-perceived severity of mastocytosis) (Hermine O, et al., 2008, PLoS ONE. 3:e2266); overall patient assessment (OPA) score; tryptase levels; and change in organ mast cell infiltration. Determination of D816V mutation and serum tryptase levels was conducted following procedures described previously (Hermine O, et al., 2008, PLoS ONE. 3:e2266). Overall clinical response analysis at W12 defined a responder as having an improvement of $\geq 50\%$ in baseline handicap of a key response endpoint (Hamilton rating, flushes, or pruritus) without deterioration or emergence of handicap. Any patient with deterioration of $\geq 50\%$ in any handicap, and/or with emergence of a new handicap with an increase of $\geq 50\%$ from baseline was considered as worsening. Any patient who discontinued the study before W12 was considered a non responder. Discrimination between dose regimens was investigated by analyses of the 'time to first response', according to the initial dosage, and 'dose at time of first response' in key response endpoints.

Safety assessment was based upon the frequency and severity of AEs, regardless of causality, with the treating physician assessing any possible relationship to treatment. Intensity of AEs was classified as being: mild (signs and symptoms are present but without functional impact); moderate (functional impact without putting the patient's health at risk); or severe (significant functional or definitive alteration or incapacity representing a risk for the patient's health).

Statistical Methods

Response analysis was performed on subgroups of the ITT population according to a patient's handicap at baseline and for whom response was evaluated at W12; referred to hereafter as the handicap-related population. No data imputation was implemented. The per protocol (PP) population was defined as a subset of a given handicap-related population, which in addition had presented no major protocol deviations. Summary response data are presented using descriptive statistics with mean improvement compared to baseline in each handicap cohort, regardless of disease classification. The appropriate Wilcoxon or Fisher tests were used for group comparison of baseline disease, demographic characteristics between dose level groups and response relative to baseline. Subpopulation analysis was also conducted according to initial c-Kit status.

Results

Baseline Characteristics and Participant Flow

A total of 25 patients with varying handicap profiles were recruited from seven centers across France between January 2005 and March 2007. Patients were diagnosed with smoldering (1/25), indolent systemic (17/25) or cutaneous mastocytosis (7/25); however, consistent with the AFIRMM concept that these subtypes form part of a continuous spectrum of mast cell-related dysfunctions, all patients were considered as a single group. Patients were randomized to receive masitinib at the initial dose of 3 mg/kg/day (N=13) or 6 mg/kg/day (N=12) for 12 weeks. There was no relevant difference in disease and demographic characteristics between dose groups except for Hamilton rating (p=0.05).

The majority of patients had a significant handicap in terms of frequency of flushes (80%), pruritus (80%) and Hamilton rating (56%); see Table 3.

Twenty-two patients (88%) completed the study, with 17/25 patients (68%) entering the study's extension phase. At the cut-off date of 31st August 2008, 8/25 patients (32%) were still undergoing treatment and had received a treatment exposure >2 years. Of the 3/25 patients (12%) who withdrew prior to W12, 2/25 patients (8%) withdrew due to occurrence of AEs and one patient was considered as lost to follow-up after withdrawing their consent to participate. All but one patient (96%) fulfilled the inclusion criterion of having at least one confirmed mast cell infiltrated organ in which mutations of the c-Kit gene including the D816V mutation were not detectable. The remaining patient carried the D816V mutation in the bone marrow but was of unknown status in the skin (a deviation from the inclusion criterion, but this patient was retained for analyses). Breakdown of c-Kit mutation status revealed that 19/25 patients (76%), (referred to hereafter as Group 1), had no confirmed D816V mutation infiltration; whilst 6/25 patients (24%), (referred to hereafter as Group 2), had at least one organ with a D816V mutation infiltration, i.e. a mixed c-Kit status. Within Group 1, 8/25 Patients (32%) Had the Wild-Type c-Kit Status Confirmed in Both Skin and bone marrow, whilst the remaining 11/25 patients (44%) had an unknown status in one or other organ.

Response Assessment

Overall, results according to a given handicap-related population and PP handicap-related population were very similar, with the former presented hereafter unless otherwise stated (Table 4). Response analyses for flushes, Hamilton rating, and pruritus showed mean improvements at W12 relative to baseline of 64%±55 (p=0.0005), 42%±30 (p=0.0049), and 36%±43 (p=0.0077), respectively. Improvement in stool and micturition frequencies were 29%±58 and 23%±30, respectively, although both showed greater improvement in the PP population of 44%±63 and 39%±14, respectively. Analysis of the QLQ-C30 questionnaire showed improvement in the global health status, functional score and symptom score of 51%±108, 39%±81 and 2.5%±69, respectively. Regarding the AFIRMM global score, evaluable patients (N=20), i.e. those for whom W12 data was available, showed an improvement of 40%±27. For the OPA score, 3/20 evaluable patients (15%) who had impaired health status at baseline reported none or minimal impairment at W12. In total, 9/20 patients (45%) reported an improvement of at least one point in their OPA score, and with the exception of just 1/20 patient (5%) at one time point, no worsening of health status was reported. Assessment of overall clinical response at W12 was evident in 14/25 patients (56%; [95% CI=37-75%]). Individually, these handicaps showed clinical response rates of 60% [95% CI=39-81%]; 50% [95% CI=24-76%]; and 25% [95% C6-44%], respectively (Table 5).

Therapeutic effect was observed as early as week 4 in all clinical symptoms associated with indolent mastocytosis handicap (Table 6), indicating a rapid onset of action. Considering this study's extension phase preliminary data (Table 6), the improvement achieved by W12 was maintained and even augmented for flushes, pruritus, Hamilton rating, micturition frequency, stool frequency, QLQ-C30 functional, QLQ-C30 global health status, AFIRMM and OPA scores. Such observations are indicative of masitinib's potency on these endpoints and its sustainability. In addition, subpopulation analyses with regards to initial c-Kit status (c-Kit Groups 1 and 2) revealed that masitinib displayed similar response patterns in both groups.

TABLE 3

Demographic profile, clinical baseline, handicap*, disposition and drug exposure, according to initial masitinib dosage (ITT population).

| | Parameter | | 3 mg/kg/day N = 13/25 | 6 mg/kg/day N = 12/25 | All N = 25/25 |
|---|---|---|---|---|---|
| Demographic | Age (years) | Mean ± SD | 40.2 ± 13.3 | 46.1 ± 18.0 | 43.0 ± 15.7 |
| | | Range | 22.0-59.0 | 20.0-76.0 | 20.0-76.0 |
| | Weight (kg) | Mean ± SD | 67.9 ± 17.5 | 67.5 ± 11.5 | 68.6 ± 14.6 |
| | | Range | 45.0-99.5 | 49.0-82.0 | 45.0-99.5 |
| | Gender | Female | 8/13 (61.5%) | 9/12 (75.0%) | 17/25 (68.0%) |
| Clinical | Pruritus | Mean ± SD | 7.1 ± 2.4 | 7.4 ± 2.6 | 7.2 ± 2.4 |
| | | Range | 0.0-10.0 | 3.5-12.5 | 0.0-12.5 |
| | Flushes (per day) | Mean ± SD | 1.8 ± 1.6 | 2.3 ± 2.5 | 2.0 ± 2.1 |
| | | Range | 0.0-5.0 | 0.0-9.0 | 0.0-9.0 |
| | Hamilton rating | Mean ± SD | 11.2 ± 3.4 | 8.6 ± 7.3 | 10.0 ± 5.7 |
| | | Range | 4.0-19.0 | 2.0-28.0 | 2.0-28.0 |
| | Stools (per day) | Mean ± SD | 2.9 ± 2.4 | 2.6 ± 3.3 | 2.8 ± 2.8 |
| | | Range | 0.0-8.0 | 0.0-10.0 | 0.0-10.0 |
| | Micturitions (per day) | Mean ± SD | 6.7 ± 2.5 | 8.8 ± 5.9 | 7.7 ± 4.5 |
| | | Range | 3.0-12.0 | 3.0-20.0 | 3.0-20.0 |
| | QLQ30 - Global health score | Mean ± SD | 40.4 ± 20.4 | 48.6 ± 20.4 | 44.3 ± 20.4 |
| | | Range | 0.0-83.3 | 16.7-100.0 | 0.0-100.0 |
| | QLQ30 - Functional score | Mean ± SD | 53.7 ± 26.2 | 65.6 ± 24.0 | 59.4 ± 25.4 |
| | | Range | 11.1-93.3 | 26.7-100.0 | 11.1-100.0 |
| | QLQ30 - Symptom score† | Mean ± SD | 43.6 ± 19.9 | 34.1 ± 18.6 | 39.2 ± 19.5 |
| | | Range | 10.3-69.2 | 2.6-59.0 | 2.6-69.2 |
| | OPA score | 0, 1 (No handicap) | 2/13 (15.4%) | 3/12 (25.0%) | 5/25 (20.0%) |
| | | 2, 3, 4 (Handicap) | 11/13 (84.6%) | 9/12 (75.0%) | 20/25 (80.0%) |
| | AFIRMM score | Mean ± SD | 176.6 ± 75.2 | 141.5 ± 92.6 | 159.8 ± 84.1 |
| | | Range | 60.0-342.0 | 34.0-298.0 | 34.0-342.0 |

TABLE 3-continued

Demographic profile, clinical baseline, handicap*, disposition and drug exposure, according to initial masitinib dosage (ITT population).

| | Parameter | | 3 mg/kg/day N = 13/25 | 6 mg/kg/day N = 12/25 | All N = 25/25 |
|---|---|---|---|---|---|
| Handicap | Pruritus ≥6 | N, % | 11/13 (85%) | 9/12 (75%) | 20/25 (80%) |
| | Flushes (per day) ≥1 | N, % | 10/13 (77%) | 10/12 (83%) | 20/25 (80%) |
| | Hamilton rating ≥10 | N, % | 11/13 (85%) | 3/12 (25%) | 14/25 (56%) |
| | Stools (per day) ≥4 | N, % | 6/13 (46%) | 4/12 (33%) | 10/25 (40%) |
| | Micturitions (per day) ≥8 | N, % | 4/13 (31%) | 6/12 (50%) | 10/25 (40%) |
| Disposition | Early study discontinuation | N, % | 3/13 (23%) | 1/12 (8%) | 4/25 (16%) |
| | Adverse event | | 2/13 (15%) | 1/12 (8%) | 3/25 (12%) |
| | Lost to follow-up | | 1/13 (8%) | 0/12 (0%) | 1/25 (4%) |
| | Completed study | N, % | 10/13 (77%) | 11/12 (92%) | 21/25 (84%) |
| | Entered extension phase | N, % | 8/13 (61%) | 9/12 (75%) | 17/25 (68%) |
| Exposure | No dose adjustment | N, % | 2/13 (15%) | 1/12 (8%) | 3/25 (12%) |
| | Dose increase | N, % | 10/13 (77%) | 3/12 (25%) | 13/25 (52%) |
| | Increment by 1/2 steps | N/N | 3/7 | 3/0 | 6/7 |
| | Dose decrease | N, % | 0/13 (0%) | 2/12 (17%) | 2/25 (8%) |
| | Decrease by 1/2 steps | N/N | 0/0 | 2/0 | 2/0 |
| | Dose increase/decrease (±1) | N, % | 1/13 (8%) | 6/12 (50%) | 7/25 (28%) |

*Refer to text for handicap definitions.
†QLQ30 - Symptom score: All (N = 24); 6 mg/kg/day (N = 11/25). Information on baseline characteristics of handicap-related population, regardless of initial dosing level, is presented in Table 4.

TABLE 4

Response at week-12 for patients with associated handicap at baseline, including subgroup analysis according to initial c-Kit status*.

| Parameter | All | Group 1 | Group 2 |
|---|---|---|---|
| Pruritus (N) | 15 | 12 | 3 |
| Baseline (Mean ± SD) | 8.1 ± 1.8 | 8.0 ± 1.8 | 8.3 ± 2.3 |
| Δ Mean ± SD | −3.0 ± 3.4 | −3.5 ± 3.6 | −1.0 ± 2.2 |
| Relative Δ Mean ± SD | −36% ± 43 | −42% ± 45 | −11% ± 27 |
| Flushes per day (N) | 17 | 13 | 4 |
| Baseline | 2.5 ± 2.1 | 2.9 ± 2.3 | 1.3 ± 0.5 |
| Δ Mean ± SD | −1.7 ± 1.5 | −2.0 ± 1.6 | −0.8 ± 0.5 |
| Relative Δ Mean ± SD | −64% ± 55 | −64% ± 59 | −63% ± 48 |
| Hamilton rating (N) | 12 | 11 | 1 |
| Baseline | 13.3 ± 5.0 | 13.0 ± 5.1 | 16.0 |
| Δ Mean ± SD | −5.1 ± 4.4 | −4.6 ± 4.3 | −10.0 |
| Relative Δ Mean ± SD | −42% ± 30 | −41% ± 31 | −63% |
| Stools per day (N) | 10 | 8 | 2 |
| Baseline | 5.6 ± 2.2 | 5.5 ± 2.3 | 6.0 ± 2.8 |
| Δ Mean ± SD | −1.9 ± 3.6 | −2.0 ± 4.0 | −1.5 ± 2.1 |
| Relative Δ Mean ± SD | −29% ± 58 | −26% ± 62 | −38% ± 53 |
| Micturitions per day (N) | 9 | 7 | 2 |
| Baseline | 11.1 ± 3.2 | 11.0 ± 3.1 | 11.5 ± 4.9 |
| Δ Mean ± SD | −3.1 ± 3.7 | −3.0 ± 2.8 | −3.5 ± 7.8 |
| Relative Δ Mean ± SD | −23% ± 30 | −25% ± 24 | −18% ± 60 |
| QLQ-C30 Functional (N) | 20 | 16 | 4 |
| Baseline | 59.2 ± 26.6 | 58.0 ± 29.4 | 63.9 ± 11.4 |
| Δ Mean ± SD | 8.7 ± 18.8 | 8.7 ± 21.0 | 8.6 ± 4.8 |
| Relative Δ Mean ± SD | 39% ± 81 | 45% ± 90 | 14% ± 9 |
| QLQ-C30 Symptom (N) | 18 | 15 | 3 |
| Baseline | 40.6 ± 19.8 | 38.6 ± 20.8 | 50.6 ± 11.3 |
| Δ Mean ± SD | −6.1 ± 13.6 | −5.4 ± 14.7 | −9.5 ± 6.2 |
| Relative Δ Mean ± SD | −2.5% ± 69 | 0.5% ± 75 | −18% ± 9 |
| QLQ-C30 Global Health (N) | 20 | 16 | 4 |
| Baseline | 45.8 ± 22.4 | 45.8 ± 24.9 | 45.8 ± 8.3 |
| Δ Mean ± SD | 12.5 ± 24.7 | 14.1 ± 27.0 | 6.3 ± 12.5 |
| Relative Δ Mean ± SD | 51% ± 108 | 60% ± 119 | 13% ± 25 |
| AFIRMM (N) | 20 | 16 | 4 |
| Baseline | 164.6 ± 81 | 173.3 ± 83.5 | 130.0 ± 68.3 |
| Δ Mean ± SD | −61.5 ± 49.6 | −63.5 ± 52.9 | −53.5 ± 38.5 |
| Relative Δ Mean ± SD | −40% ± 27 | −40% ± 27 | −43% ± 29 |
| OPA Score# (N) | 20 | 16 | 4 |
| Change: (2, 3, 4) to (0, 1) | 3/20 (15%) | 3/16 (19%) | 0/4 (0%) |
| No change | 16/20 (80%) | 12/16 (75%) | 4/4 (100%) |
| Change: (0, 1) to (2, 3, 4) | 1/20 (5%) | 1/16 (6%) | 0/4 (0%) |

*Refer to text for handicap and c-Kit group status definitions. Each handicap-related population is a subgroup of the ITT population according to a patient's handicap at baseline and for whom response was evaluated at week 12.
N = number of patients in given cohort.
Δ Mean = change in population's mean handicap score compared to the corresponding population's baseline.
OPA score (2, 3, 4) = impaired health status; OPA score (0, 1) = none or minimal impairment.

TABLE 5

Clinical response rates (improvement of ≥50% in handicap at W12 relative to baseline).

| | Pruritus | Flushes | Hamilton |
|---|---|---|---|
| Handicap (W0), N | 20 | 20 | 14 |
| No Handicap (W0), N | 5 | 5 | 11 |
| Responders (W12) | 5/20 (25%) | 12/20 (60%) | 7/14 (50%) |
| [95% CI] | 6-44% | 39-81% | 24-76% |
| Non responders (W12) | | | |
| Stable handicap | 12/20 (60%) | 4/20 (20%) | 5/14 (36%) |
| Discontinued | 3/20 (15%) | 3/20 (15%) | 2/14 (14%) |

TABLE 5-continued

Clinical response rates (improvement of ≥50% in handicap at W12 relative to baseline).

| | Pruritus | Flushes | Hamilton |
|---|---|---|---|
| Worsening | 0/20 (0%) | 1/20 (5%) | 0/14 (0%) |
| Emergent | 0/5 (0%) | 1/5 (20%) | 1/11 (9%) |

Responder defined as having an improvement of ≥50% in baseline handicap. Overall clinical response rate (improvement of ≥50% in baseline handicap of Hamilton rating, flushes, or pruritus, without deterioration or emergence of a handicap) was observed in 14/25 patients (56%; [95% CI = 37%-75%])

Of the 15 patients evaluable for reduction in bone marrow mast cell infiltration, i.e. biopsies carried out at baseline and W12, one patient showed a reduction in bone marrow mast cell infiltration from 7% at baseline to 1% at W12. Mast cell reduction in the 14 patients evaluable for skin infiltration showed 1/14 patient (7%) experienced a good partial response (≥50% reduction), 6/14 patients (43%) experienced a partial response (1 to 49% reduction), and the remaining 7/14 patients (50%) had no change. Analysis of tryptase level at W12 in the overall PP population, showed a mean reduction of 23% in patients possessing elevated tryptase (>15 ng/mL) at baseline (N=5). Analysis of time to first response showed no clear difference between the randomized initial dosing groups. Analysis of dose at time of first response (Table 7) revealed that 76/79 first response events (96%) occurred at a dose ≤6 mg/kg/day. The next dose increment to 7.5 mg/kg/day generated only minor gains, whilst the lower dose level of 4.5 mg/kg/day showed a reduction in number of response events to just 48/79 (60%).

TABLE 7

Dose at time of first response.

| Dose (mg/kg/day) | A | B | C | D | E | F | G | H | I | L | M | N |
|---|---|---|---|---|---|---|---|---|---|---|---|---|
| 1.5 | | | | | | | | | | | 0 | 0 |
| 3.0 | 5 | 9 | 4 | 5 | | 2 | 3 | 2 | 2 | 4 | 36 | 46 |
| 4.5 | 2 | 3 | 2 | | | 2 | 1 | 1 | | 1 | 12 | 61 |
| 6.0 | 4 | 4 | 4 | 2 | 1 | 2 | 1 | 1 | 4 | 5 | 28 | 96 |
| 7.5 | | 1 | | | | | | 1 | 1 | | 3 | 100 |
| Total | 11 | 17 | 10 | 7 | 1 | 6 | 5 | 5 | 7 | 10 | 79 | |

Response defined as having an improvement of ≥50% in baseline handicap between weeks W0 to W12.
In Table 7:
Column A = Pruritus
Column B = Flush
Column C = Hamilton
Column D = Stool
Column E = Micturition
Column F = QLQ30 Global
Column G = QLQ30 Functional
Column H = QLQ30 Symptom
Column I = OPA score
Column L = AFIRMM score
Column M = Total events
Column N = Cumulative Frequency (%)

TABLE 6

Change of efficacy outcomes including the study's extension phase up to week 60.

| Parameter | W4 | W12 | W24 | W36 | W48 | W60 |
|---|---|---|---|---|---|---|
| Pruritus (N) | 14 | 12 | 10 | 7 | 6 | 9 |
| ΔMean ± SD | -2.8 ± 3.7 | -3.3 ± 3.0 | -5.1 ± 4.7 | -6.9 ± 3.5 | -5.2 ± 4.4 | -4.6 ± 4.3 |
| Relative Δ Mean ± SD | -33% ± 44 | -39% ± 38 | -57% ± 48 | -79% ± 41 | -56% ± 40 | -50% ± 42 |
| Flushes per day (N) | 13 | 14 | 11 | 9 | 8 | 9 |
| ΔMean ± SD | -1.1 ± 1.8 | -1.6 ± 1.5 | -1.9 ± 3.1 | -2.1 ± 3.5 | -2.8 ± 2.9 | -2.3 ± 2.9 |
| Relative Δ Mean ± SD | -32% ± 95 | -57% ± 59 | -34% ± 128 | -67% ± 100 | -88% ± 35 | -67% ± 66 |
| Hamilton rating (N) | 9 | 9 | 4 | 3 | 2 | 3 |
| ΔMean ± SD | -5.9 ± 3.2 | -4.6 ± 4.9 | -2.8 ± 9.2 | -10.3 ± 5.1 | -11.5 ± 6.4 | -8.3 ± 7.5 |
| Relative Δ Mean ± SD | -44% ± 23 | -37% ± 33 | -15% ± 66 | -72% ± 27 | -77% ± 33 | -57% ± 45 |
| Stools per day (N) | 4 | 5 | 4 | 3 | 2 | 3 |
| ΔMean ± SD | -4.3 ± 2.6 | -4.2 ± 3.0 | -2.5 ± 2.1 | -0.7 ± 3.2 | -2.0 ± 0.0 | -4.7 ± 2.9 |
| Relative Δ Mean ± SD | -81% ± 24 | -66% ± 38 | -47% ± 33 | -17% ± 80 | -50% ± 0 | -83% ± 14 |
| Micturitions per day (N) | 4 | 5 | 3 | 2 | 2 | 2 |
| ΔMean ± SD | -2.5 ± 3.3 | -5.4 ± 2.6 | -4.3 ± 5.9 | -6.5 ± 6.4 | -7.0 ± 2.8 | -6.0 ± 4.2 |
| Relative Δ Mean ± SD | -15% ± 28 | -41% ± 15 | -30% ± 38 | -45% ± 40 | -47% ± 19 | -49% ± 16 |
| QLQC30 Functional (N) | 17 | 15 | 4 | 5 | 6 | 9 |
| ΔMean ± SD | 8.7 ± 18.2 | 11.6 ± 16.4 | 15.3 ± 10.6 | 5.8 ± 16.7 | 0.7 ± 16.7 | 11.6 ± 11.2 |
| Relative Δ Mean ± SD | 45% ± 98 | 48% ± 89 | 74% ± 112 | 22% ± 55 | -1.3% ± 26 | 15% ± 16 |
| QLQC30 Symptom (N) | 17 | 14 | 4 | 5 | 6 | 9 |
| ΔMean ± SD | -4.1 ± 7.8 | -7.0 ± 15.2 | -19.9 ± 8.2 | -14.4 ± 6.5 | -10.3 ± 6.4 | -12.9 ± 8.3 |
| Relative Δ Mean ± SD | 3.1% ± 59 | -1.4% ± 78 | -54% ± 23 | -46% ± 34 | -36% ± 25 | -33% ± 90 |
| QLQC30 Global Health (N) | 17 | 15 | 4 | 5 | 6 | 9 |
| ΔMean ± SD | 8.3 ± 25.5 | 16.1 ± 26.4 | 18.8 ± 27.5 | 21.7 ± 26.1 | 12.5 ± 14.7 | 23.1 ± 25.3 |
| Relative Δ Mean ± SD | 26% ± 85 | 66% ± 121 | 71% ± 111 | 87% ± 126 | 36% ± 43 | 69% ± 96 |
| AFIRMM (N) | 17 | 15 | 3 | 5 | 6 | 9 |
| ΔMean ± SD | -44.5 ± 51.6 | -61.9 ± 45.9 | -66.0 ± 29.9 | -62.4 ± 31.8 | -64.3 ± 48.5 | -61.1 ± 32.9 |
| Relative Δ Mean ± SD | -33% ± 34 | -44% ± 27 | -39% ± 20 | -55% ± 27 | -49% ± 34 | -62% ± 21 |
| OPA Score[#] (N) | 17 | 15 | 3 | 5 | 6 | 9 |
| Change: (2, 3, 4) to (0, 1) | 3 (18%) | 3 (20%) | 0 (0%) | 1 (20%) | 2 (33%) | 4 (44%) |
| No change | 14 (82%) | 16 (80%) | 3 (100%) | 4 (80%) | 4 (67%) | 5 (56%) |

Each handicap-related population (N) consists of patients who entered the extension phase having a given handicap at baseline and for whom efficacy was evaluated at the relevant time point.
Δ Mean = change in population's mean handicap score compared to the corresponding population's baseline.
[#]OPA score (2, 3, 4) = impaired health status; OPA score (0, 1) = none or minimal impairment. Baseline OPA scores: (0, 1) 5/25 patients (20%), (2, 3, 4) 20/25 patients (80%).

TABLE 8

Number of patients (%) with at least one suspected adverse event (≥10%) during the initial study phase, according to dose (mg/kg/day) at AE onset.

| System Organ Class/Preferred Term[†] | A | B | C | D | E | F | G |
|---|---|---|---|---|---|---|---|
| At least one suspected AE | 21 / 84.0% | 1 / 20.0% | 9 / 64.3% | 11 / 61.1% | 12 / 60.0% | 2 / 25.0% | 1 / 33.3% |
| Nausea/Vomiting | 13 / 52.0% | | 5 / 35.7 | 7 / 38.9 | 3 / 15.0 | 1 / 12.5 | |
| Nausea | 11 / 44.0% | | 4 / 28.6% | 6 / 33.3% | 2 / 10.0% | 1 / 12.5% | |
| Edema - all categories | 11 / 44.0% | | 1 / 7.1% | 3 / 16.7% | 7 / 35.0% | 1 / 12.5% | |
| Muscle spasms | 7 / 28.0% | | 1 / 7.1% | 3 / 16.7% | 3 / 15.0% | 1 / 12.5% | |
| Rash - all categories | 7 / 28.0% | | 3 / 21.4% | | 5 / 25.0% | | 1 / 33.3% |
| Asthaenia | 6 / 24.0% | | 1 / 7.1% | 2 / 11.1% | 3 / 15.0% | 1 / 12.5% | |
| Vomiting | 5 / 20.0% | | 1 / 7.1% | 3 / 16.7% | 1 / 5.0% | 1 / 12.5% | |
| Headache | 5 / 20.0% | | 2 / 14.3% | 2 / 11.1% | 1 / 5.0% | | |
| Abdominal pain | 4 / 16.0% | | | 2 / 11.1% | 2 / 10.0% | | |
| Diarrhea | 3 / 12.0% | | | 1 / 5.6% | 2 / 10.0% | 1 / 12.5% | |
| Eructation | 3 / 12.0% | | | 1 / 5.6% | 2 / 10.0% | | |
| Dyspnea | 3 / 12.0% | | 1 / 7.1% | 1 / 5.6% | 1 / 5.0% | | |

Due to the possibility of dose adjustment a given patient may have experienced a given AE at more than one dose level.
[†]MedDRA terminology.
In Table 8:
Column A = All patients (N = 25)
Column B = 1.5 (mg/kg/day) (N = 5)
Column C = 3.0 (mg/kg/day) (N = 14)
Column D = 4.5 (mg/kg/day) (N = 18)
Column E = 6.0 (mg/kg/day) (N = 20)
Column F = 7.5 (mg/kg/day) (N = 8)
Column G = 9.0 (mg/kg/day) (N = 3)

Safety Assessment

At the cut-off date, 21/25 patients (84%) had reported at least one suspected masitinib-related AE. The most common (≥10%) treatment-related AEs are presented in Table 8, including: nausea/vomiting (52%), edema (44%), nausea (44%), muscle spasms (28%), and rash (28%). The incidence of treatment related AEs according to intensity is presented in Table 9 for the initial and extension phases. The majority of AEs experienced during the initial 12-week phase were of mild to moderate intensity. All severe AEs recovered spontaneously or with symptomatic treatments. Two treatment-related SAEs were reported in one patient who experienced two episodes of agranulocytosis at a dose of 3 mg/kg/day. The first episode occurred in the fourth week of treatment and resolved within 2 weeks of drug withdrawal. Reintroduction of masitinib led to a progressive reduction of neutrophils count within 9 days, prompting an early termination of treatment. Two other patients discontinued the study early after experiencing AEs of mild to moderate intensity, i.e. a total of 3/25 patients (12%) discontinued treatment due to AEs. No deaths occurred during this study. A decrease in the occurrence and severity of AEs was evident for patients entering the extension phase (Table 9). Specifically, no incidence of skin rash was reported after W12 and a reduction in the incidence of nausea/vomiting (52% versus 18%), edema (44% versus 6%), and nausea (44% versus 12%), were observed between the initial and extension phases, respectively.

Discussion

Results indicate that the compound of the invention (i.e. a tyrosine kinase inhibitor or a mast cell inhibitor, especially masitinib or a pharmaceutically acceptable salt or solvate thereof), significantly reduced disability in adult patients suffering from indolent forms of mastocytosis with handicap during a 12-week treatment period. Overall, an improvement in quality-of-life was evidenced via the patients' reported outcomes. Only the QLQ-C30 symptom score showed a relatively modest improvement but this discrepancy may be due to interference from masitinib's gastrointestinal safety profile.

Similar response patterns were evident regardless of initial c-Kit status (Groups 1 and 2), that is to say, in both D816V positive and D816V negative mastocytosis patients. This observation indicates that a confirmed presence of the D816V mutation does not adversely affect a tyrosine kinase inhibitor or a mast cell inhibitor, especially masitinib treatment of indolent mastocytosis with handicap.

A tyrosine kinase inhibitor or a mast cell inhibitor, especially masitinib, may therefore prove effective in treatment of indolent mastocytosis associated with D816V mutation. A possible explanation for the observation that masitinib can provide effective treatment of indolent mastocytosis associated with D816V mutation is that masitinib's inhibitory action on Lyn/Fyn also plays a significant role in controlling mast cell degranulation and hence handicap, independent of the c-Kit signaling pathway and survival of mast cells.

Although occurrence of AEs was relatively high (84%) over the first 12 weeks, the majority of these were of mild or moderate severity and in general occurred early during the course of treatment, which is consistent with the known safety profile of tyrosine kinase inhibitors. This trend, albeit from a relatively small population size, is evident when comparing safety data from the initial and extension phases. The implication is that whilst masitinib is not completely free from side-effects, the majority are manageable with appropriate symptomatic treatments and with good tolerance experienced after W12 and during any long-term treatment regimen. One patient experienced agranulocytosis, which resolved upon drug withdrawal with positive rechallenge. Myelosuppression is a known complication of other tyrosine kinase inhibitors such as imatinib, which has been associated with grade 4 neutropaenia in 5% of patients. Monitoring of blood cell count will therefore be necessary in phase 3 studies with masitinib.

The initial dose randomization undertaken in this study was conducted with an objective to determine optimal dosing of masitinib in indolent mastocytosis with handicap. Based upon analyses of dose at time of first response and frequency of AEs according to dose, an initial dose of 6 mg/kg/day administered in two daily intakes is recommended; providing an acceptable balance between therapeutic benefit and risk.

Results from this proof-of-concept study indicate that symptomatic resistant handicaps associated with indolent mastocytosis, and regardless of D816V c-Kit mutation status (i.e. in both D816V positive and D816V negative mastocytosis patients), are manageable with a tyrosine kinase inhibitor or a mast cell inhibitor, especially masitinib over a long duration of time.

Example 2

Phase II Study of Masitinib in Patients with Systemic Indolent or Cutaneous Mastocytosis, with Mast Cell Mediator Release Associated Handicap and Bearing Activating Point Mutations in the Phosphotransferase Domain of c-Kit Such as the Main Mutation Asp-816-Val (D816V)

Methods

Study Design

This study was to investigate whether masitinib could reduce mast cell mediator release associated handicap in patients having indolent mastocytosis bearing activating point mutations in the phosphotransferase domain of c-Kit such as the main mutation Asp-816-Val (D816V). The study was a phase 2a, multicenter, non-controlled, open-label trial, evaluating the efficacy and safety of oral masitinib administered at 3 or 6 mg/kg/day for 12 weeks, with an extension phase possible for those patients experiencing improvement. Dose ranging was performed by randomly assigning patients

TABLE 9

Number of subjects (%) with at least one suspected adverse event, according to intensity.

| Initial Phase (>10%) System Organ Class/Preferred Term[†] | All (N = 25) | Mild | Moderate | Severe |
|---|---|---|---|---|
| At least one suspected AE* | 21 (84.0%) | 11 (44.0%) | 19 (76.0%) | 9 (36.0%) |
| Nausea/Vomiting | 13 (52.0%) | 6 (24.0%) | 8 (32.0%) | 1 (4.0%) |
| Nausea | 11 (44.0%) | 5 (20.0%) | 7 (28.0%) | 1 (4.0%) |
| Edema - all categories | 11 (44.0%) | 3 (12.0%) | 8 (32.0%) | 2 (8.0%) |
| Muscle spasms | 7 (28.0%) | 1 (4.0%) | 7 (28.0%) | 1 (4.0%) |
| Rash - all categories | 7 (28.0%) |  | 6 (24.0%) | 2 (8.0%) |
| Asthaenia | 6 (24.0%) |  | 4 (16.0%) | 3 (12.0%) |
| Vomiting | 5 (20.0%) | 1 (4.0%) | 4 (16.0%) |  |
| Headache | 5 (20.0%) |  | 5 (20.0%) |  |
| Abdominal pain | 4 (16.0%) | 2 (8.0%) | 3 (12.0%) |  |
| Diarrhea | 3 (12.0%) | 1 (4.0%) | 2 (8.0%) | 1 (4.0%) |
| Eructation | 3 (12.0%) |  | 2 (8.0%) | 1 (4.0%) |
| Dyspnoea | 3 (12.0%) |  | 3 (12.0%) |  |

| Extension phase (>5%) System Organ Class/Preferred Term | All (N = 17) | Mild | Moderate | Severe |
|---|---|---|---|---|
| At least one suspected AE | 10 (58.8%) | 6 (35.3%) | 5 (29.4%) | 1 (5.9%) |
| Nausea/Vomiting | 3 (17.6%) | 2 (11.8%) | 1 (5.9%) |  |
| Nausea | 2 (11.8%) | 2 (11.8%) |  |  |
| Blepharitis | 1 (5.9%) | 1 (5.9%) |  |  |
| Abdominal pain | 1 (5.9%) |  | 1 (5.9%) |  |
| Aphthous stomatitis | 1 (5.9%) |  |  | 1 (5.9%) |
| Gingivitis | 1 (5.9%) | 1 (5.9%) |  |  |
| Vomiting | 1 (5.9%) |  | 1 (5.9%) |  |
| Cytolytic hepatitis | 1 (5.9%) |  | 1 (5.9%) |  |
| Gamma-glutamyltransferase increased | 1 (5.9%) | 1 (5.9%) |  |  |
| Arthralgia | 1 (5.9%) | 1 (5.9%) |  |  |
| Muscle spasms | 1 (5.9%) |  | 1 (5.9%) |  |
| Dermatitis psoriasiform | 1 (5.9%) | 1 (5.9%) |  |  |
| Eczema | 1 (5.9%) |  | 1 (5.9%) |  |
| Edema—all categories | 1 (5.9%) | 1 (5.9%) |  |  |

*AE intensity count is cumulative. AEs are recorded once only according to their start date.
[†]MedDRA terminology.

(1:1 ratio) into initial treatment groups of 3 or 6 mg/kg/day. Masitinib, supplied as 100 and 200 mg tablets (AB Science, France), was administered orally in two daily intakes. Dose adjustments of 1.5 mg/kg/day were permitted, with the dosage being incremented in case of insufficient response accompanied by minimal toxicity (mild/moderate) at weeks 4 and 8. In the event of severe toxicity, masitinib was temporarily interrupted and then resumed at the same dosage upon recovery. If toxicity persisted, treatment was interrupted until the adverse event (AE) was resolved, followed by a reduction in masitinib dosage or treatment discontinuation.

Patients

Eligible patients were aged >18 years, had previously documented indolent systemic, smoldering systemic or cutaneous mastocytosis as per the WHO classification with associated disability as the result of mast cell released mediators. Patients had to have a positive D816V c-Kit mutation status, i.e. documented presence of D816V mutation in at least one infiltrated organ including bone marrow or skin. For patients with prior documented presence of D816V mutation in at least one infiltrated organ (bone marrow or skin), no test was performed at the screening visit; however, for those patients without such documentation it was necessary to perform c-Kit molecular analysis prior to randomization. Skin biopsy and optionally (unless patients had no cutaneous lesion) a bone marrow aspirate or biopsy, were performed at baseline to confirm the presence of D816V mutation and to count mast cells in the infiltrated organs. All skin biopsies, bone marrow aspirate or biopsies, performed for this study were sent to the AB Science central laboratory for sequencing and mast cell counting. Patients were classified as having a handicap if after appropriate symptomatic treatments they fulfilled at least one of the following a priori criteria: number of flushes/week $\geq 7$; pruritus score $\geq 6$; number of stools $\geq 4$/day (i.e. diarrhea); micturition frequency $\geq 8$/day (i.e. pollakiuria); Hamilton rating for depression $\geq 10$; Fatigue Impact Scale (FIS) score $\geq 40$; or EORTC quality-of-life questionnaire (QLQ-C30) score $\geq 60$. Patients were excluded if they experienced inadequate organ function defined via blood test levels, or an Eastern Cooperative Oncology Group performance status >2. Other exclusion criteria included: life expectancy <6 months, severe or uncontrolled medical disease, and patients who were pregnant or nursing.

Efficacy and Safety

In accordance to the AFIRMM study (Hermine O, et al., 2008, PLoS ONE. 3:e2266), evaluation of treatment response was based upon the change of clinical symptoms associated with a patient's handicaps at week 12 relative to baseline. Efficacy was assessed on the symptoms of mastocytosis. Primary efficacy endpoints were treatment effect on the pruritus score, the number of flushes per week, the Hamilton score, and the Fatigue Impact scale. A patient was classified as responder if he showed improvement of $\geq 50\%$ in at least one of the main handicaps (primary endpoints), without worsening of more than 50% of any handicap and without emergence of a new handicap with an increase of more than 50% from baseline. Safety assessment was based upon the frequency and severity of AEs, regardless of causality, with the treating physician assessing any possible relationship to treatment.

Results

Baseline Characteristics

A total of 21 patients were randomized (6 male patients [29%]; 15 female patients [71%]) with all patients having a positive D816V c-Kit mutation status in at least one organ. Age range: 19-68 year-old; 18-65 year-old: 20 patients (95%); >65 year-old: 1 patient (5%). Patients presenting with mast cell mediator release associated handicap as baseline included:
- 21 patients (100%) with pruritus score $\geq 6$,
- 14 patients (66%) with Hamilton rating for depression $\geq 10$,
- 10 patients (48%) with micturition frequency $\geq 8$/day,
- 10 patients (48%) with FIS score $\geq 40$,
- 8 patients (38%) with number of stools $\geq 4$/day,
- 7 patients (33%) with number of flushes/week $\geq 7$.

Efficacy Assessment

At the cut-off date of September 2009, a total of 20 patients (95%) had completed 12 weeks of treatment, one patient (5%) withdrew prematurely prior to any evaluation under treatment and 15 patients (71%) entered the study's extension phase. The efficacy of treatment was evaluated at 12 weeks in the per protocol (PP) population (20 patients). One patient was excluded from the analyses due to study discontinuation. According to the Clinical Response definition, the overall response rate was 70% (14 of 20 patients) and four patients (20%) remained stable. The main observed improvements at week 12 relative to baseline were:
- A mean reduction of FIS score by 51.8% in the PP population (a reduction of 45.6% in the sub-population of patients with this handicap at baseline).
- A mean reduction of pruritus score by 46.0% in the PP population (all patients presented with pruritus handicap at baseline).
- A mean reduction in the frequency of flushes of 45.5% in the PP population (a reduction of 55.3% in the sub-population of patients with this handicap at baseline).
- In addition, Hamilton score was improved by 27.0% in the PP population (44.3% in the sub-population of patients with this handicap at baseline).

In addition, for patients suffering from diarrhea and pollakiuria at baseline, the daily number of stools and micturition were significantly reduced by 41.3% and 30.3%, respectively at week 12. Overall, patient assessment and quality of life (assessed by the EORTC QLQ C-30) improved consistently and the AFIRMM score (encompassing 38 mastocytosis-related symptoms) was reduced by 32.0%. Five of the patients receiving treatment on the study's extension phase had been successfully treated for more than 15 months. Their response at week 12 was maintained or improved, suggesting that the efficacy of masitinib could be sustainable.

Safety Assessment

At the cut-off date of Aug. 31, 2009, 20 patients (95%) had experienced at least one adverse event suspected to be related to masitinib. Two patients (9%) had at least one serious adverse event suspected to be related to masitinib (vomiting and headache for one patient and depressive syndrome for the other). Five patients (24%) discontinued treatment because of at least one adverse event suspected to be related to masitinib. Two patients presented with adverse event that led to dose reduction and suspected to be related to masitinib.

Conclusion

Results show that 70% of patients diagnosed with indolent forms of mastocytosis bearing the D816V c-Kit mutation reported an improvement in their baseline mast cell mediator release associated handicaps of $\geq 50\%$ following 12 weeks of treatment with the compound of the invention (i.e. a tyrosine kinase inhibitor or a mast cell inhibitor, especially masitinib or a pharmaceutically acceptable salt or solvate thereof). Evidence from the extension phase indicates that this improvement is sustainable over at least 15 months. Accordingly, a tyrosine kinase inhibitor or a mast cell inhibitor, especially masitinib is considered to be active in the treatment of indolent mastocytosis with mast cell mediator release associated handicap, and in particular for human patients with WHO-defined cutaneous or systemic mastocytosis with a positive D816V c-Kit mutation status.

Taken together, these two phase 2 studies provide evidence that a tyrosine kinase inhibitor or a mast cell inhibitor, especially masitinib is a viable therapeutic strategy for indolent mastocytosis, capable of reducing symptoms and severity of mast cell mediator release associated handicap in patients with both positive and negative D816V c-Kit mutation status. Furthermore, as patients in all categories of mastocytosis often experience symptoms from the constitutive activation of mast cells and release of their mediators it is reasonable to conclude that a tyrosine kinase inhibitor or a mast cell inhibitor, especially masitinib, optionally administered in combination with at least one other cytoreductive or disease modifying drug, can also provide therapeutic benefit across the range of mastocytosis categories, including aggressive forms of mastocytosis.

Example 3

Appraisal of Restricted Mast Cell Mediator Release Associated Handicap Population and More Stringent Response Criterion There is a debate within the mastocytosis research community concerning the need to revise the classification for mast cell disease, its diagnostic and response criteria, and recommended approaches for treatment. The cornerstone for defining disease classification, diagnosis, response criteria and treatment has been the World Health Organization (WHO) classification system; however, the underlying philosophy of this system is highly geared towards aggressive variants of mastocytosis and is of less relevance to the indolent, non-aggressive, forms of the disease. This latter group represents more than 90% of all mastocytosis cases and although the majority of these patients can expect a normal life expectancy, the associated mast cell mediator release symptoms they endure have a negative effect upon quality-of-life to the point of being disabling. Such limitations were highlighted by the AFIRMM (Association Française pour les Initiatives de Recherche sur le Mastocyte et les Mastocytoses) study of disability in 363 mastocytosis patients with indolent variants of mastocytosis [Hermine O, et al., PLoS ONE. 2008; 3:e2266]. In this population the main treatment objective is to improve a patient's quality-of-life by reducing the impact of mast cell mediator release symptoms. Data from that study revealed the majority of indolent mastocytosis patients suffer from disabilities (i.e. mast cell mediator release associated handicaps) due to the disease and that objective and subjective measures of disabilities did not differ according to disease classification, D816V c-Kit mutational status, or an elevated (≥20 ng/mL) serum tryptase level. It was also concluded that there is a need to develop treatment guidelines that are primarily based upon clinical signs rather than laboratory biomarkers. Indeed, treatment of indolent forms of mastocytosis should aim to improve the patient's quality-of-life with treatment being dictated by patient defined handicap according to mast cell mediator release symptoms. Such treatment assessment has been illustrated in examples 1 and 2 [Paul C et al. Am. J. Hematol. 85:921-925, 2010].

The clinical challenges in assessing and treating indolent forms of mastocytosis according to handicap associated with mast cell mediator release include:
1) identifying a clinically relevant mast cell mediator release associated handicap population;
2) identifying clinically significant treatment effects from a heterogeneous baseline;
3) distinguishing between treatment related benefits and placebo effect.

One way to address these challenges is to define a more specific mast cell mediator release associated handicap population via the individual handicap threshold criteria. This effectively defines a restricted population with greater disability at baseline. Another strategy would be to impose a stricter response criterion, which will ensure that any therapeutic benefit is of greater clinical significance and also will reduce the impact of placebo derived changes (i.e. false positives).

A Posteriori Analysis for Identification of a Restricted Handicap Population and Definition of a More Robust Response Criterion Of relevance to the invention described, the concepts of a restricted mast cell mediator release associated handicap population and a more stringently defined response criterion have been explored via a posteriori data analysis of a common study population. This population is derived from that of the phase 2 study presented in example 2, (i.e. masitinib treatment in patients with systemic indolent or cutaneous mastocytosis, with mast cell mediator release associated handicap and bearing activating point mutations in the phosphotransferase domain of c-Kit such as the main mutation D816V), and therefore has near identical treatment regimen and inclusion/exclusion criteria. (Note, any discrepancies between directly equivalent data presented in example 2 and example 3 are due to the former being taken from preliminary data analysis and the latter being extended/validated data from that study).

From these ad-hoc analyses we have identified a population group for whom treatment with masitinib is demonstrated to yield similar response rates but for which the therapeutic benefits are of even greater clinical significance, as compared to the original handicap thresholds and response criteria used in the phase 2 study. Specifically, the Hamilton rating for depression score at baseline is increased to 14 (from a score of 10 in example 2) and the baseline Fatigue Impact Scale score is increased to 75 (from a score of 40 in example 2).

A posteriori data analysis was carried out on a new, restricted mast cell mediator release associated handicap population (wherein patients were classified as having a handicap if after appropriate symptomatic treatments they fulfilled at least one of the following criteria: number of flushes/week ≥7; pruritus score ≥6; number of stools ≥4/day (i.e. diarrhea); micturition frequency ≥8/day (i.e. pollakiuria); Hamilton rating for depression ≥14; Fatigue Impact Scale (FIS) score ≥75; or EORTC quality-of-life questionnaire (QLQ-C30) score ≥60). This was compared directly to the same study population as defined by the original mast cell mediator release associated handicap thresholds of example 2 (number of flushes/week ≥7; pruritus score ≥6; number of stools ≥4/day (i.e. diarrhea); micturition frequency ≥8/day (i.e. pollakiuria); Hamilton rating for depression ≥10; Fatigue Impact Scale (FIS) score ≥40; or EORTC quality-of-life questionnaire (QLQ-C30) score ≥60).

Evaluation of treatment response was based upon the change of clinical symptoms in a patient's mast cell mediator release associated handicaps at week 12 relative to baseline. A breakdown of the individual mast cell mediator release associated handicaps at baseline for the new handicap criteria included:

- 21 patients (100%) with pruritus score ≥6,
- 10 patients (48%) with Hamilton rating for depression ≥14,
- 10 patients (48%) with micturition frequency ≥8/day,
- 10 patients (48%) with FIS score ≥75,
- 8 patients (38%) with number of stools ≥4/day,
- 7 patients (33%) with number of flushes/week ≥7.

Comparing the Hamilton rating for depression threshold of ≥14 (new criterion) with that of a threshold at ≥10 (original criterion), shows the number of patients that would be considered as presenting with depression was n=10 versus n=15, respectively (see Table 10). In other words, five patients failed to satisfy the elevated threshold of ≥14. Comparing the Fatigue Impact Scale (FIS) score threshold of ≥75 (new criterion) with that of a threshold at ≥50 (original criterion) shows the number of patients that would be considered as presenting with asthenia was n=10 versus n=13, respectively (see Table 10). In other words, three patients failed to satisfy the elevated threshold of ≥75. However, under the new mast cell mediator release associated handicap thresholds of this a posteriori analysis (i.e. Hamilton rating for depression ≥14, and Fatigue Impact Scale (FIS) score ≥75), all patients (n=21) were classified as having a handicap. Therefore, imposition of these higher mast cell mediator release associated handicap thresholds (representing a more severely handicapped population than compared with the original handicap thresholds) has relatively little impact on the overall population's handicap status. The implication is that the majority of mastocytosis patients will present concomitant mast cell mediator release associated handicaps in addition to depression and asthenia.

There are currently no well-established response criteria for assessing the therapeutic benefits of a treatment in an indolent mastocytosis population with respect to improvement in their mast cell mediator release associated symptoms or handicaps. The comparative phase 2 study (presented in example 2) originally defined a responder as a patient reporting an improvement of ≥50% in at least one handicap selected from flushes, pruritus, depression, or fatigue; without worsening of more than 50% of these handicaps and without emergence of a new handicap with an increase of more than 50% from baseline. In order to define a more clinically robust response criterion, and thereby distinguish better any treatment effect, our ad-hoc data analysis identified a suitable, even preferable, responder definition to be a patient reporting an improvement ≥75% in at least one baseline handicap selected from flushes, pruritus, or fatigue, or an improvement of at least two categories in the Hamilton rating scale for depression. This change from baseline represents a highly clinically relevant improvement. The responder status of the patient will be invalidated if the patient presents a worsening of more than 50% of any baseline handicap among pruritus, flushes and fatigue with a score above the handicap threshold or a worsening of at least two categories (or at least one category for patients with severe depression at baseline) of the Hamilton rating scale for depression.

The response for individual parameters is presented in Table 10. Comparing the new handicap thresholds and response criterion with that of the original handicap thresholds and response criterion, shows the number of patients that would be considered as responders (i.e. overall response rate) was n=11(52%) versus n=14 (62%), respectively. In other words, three patients failed to satisfy the new, elevated criteria.

TABLE 10

A posteriori analysis of new clinical response and handicap criteria (improvement of ≥75% in handicap at W12 relative to baseline; mast cell mediator release associated handicap thresholds: number of flushes/week ≥7; pruritus score ≥6; Hamilton rating for depression (Ham) ≥14; Fatigue Impact Scale (FIS) score ≥75), compared with the original response and handicap criteria.

|  | New Response/Handicap criteria | | | | Original Response/Handicap criteria | | | |
| --- | --- | --- | --- | --- | --- | --- | --- | --- |
|  | [A] | [B] | [C] | [D] | [A] | [B] | [C] | [D] |
| Disability (W0), N | 21 | 7 | 10 | 10 | 21 | 7 | 15 | 13 |
| Responders (W12), N, % | 8 (38%) | 4 (57%) | 3 (30%) | 1 (10%) | 8 (38%) | 4 (57%) | 7 (47%) | 4 (31%) |
| Non responders (W12) | 11 (52%) | 3 (43%) | 5 (50%) | 9 (90%) | 11 (52%) | 3 (43%) | 5 (33%) | 9 (69%) |
| Stable disease | 11 (52%) | 3 (43%) | 5 (50%) | 9 (90%) | 11 (52%) | 3 (43%) | 5 (33%) | 9 (69%) |
| Worsening disease | 0 (0%) | 0 (0%) | 0 (0%) | 0 (0%) | 0 (0%) | 0 (0%) | 0 (0%) | 0 (0%) |
| Non assessable* | 2 (10%) | 0 (0%) | 2 (20%) | 0 (0%) | 2 (10%) | 0 (0%) | 3 (20%) | 0 (0%) |
| No Disability (W0), N | 0 | 14 | 11 | 11 | 0 | 14 | 6 | 8 |
| Emergent | 0 (0%) | 1 (7%) | 1 (9%) | 0 (0%) | 0 (0%) | 1 (7%) | 1 (17%) | 0 (0%) |

In Table 10:
[A] = Pruritus
[B] = Flushes
[C] = Ham
[D] = FIS

Other Proposed Response Criterion of Note

In addition to the more stringent response criterion described above, a number of other definitions for the response criteria can be considered.

i) A cumulative response criterion, which reflects the relief of the patient's handicap burden over the treatment period, (i.e. defined as the number of assessment visits for which a response is observed divided by the number of assessment visits in total).

ii) A sustained or confirmed response criterion, defined as the proportion of patients showing a response on at least two consecutive assessment visits over the treatment period, reflecting durability of the response.

iii) Response on at least two baseline handicaps among pruritus, flushes, depression and fatigue, defined as a responder reporting a given response (e.g. 75%) in at least two baseline handicaps, without worsening of more than 50% of these handicaps and without emergence of a new handicap with an increase of more than 50% from baseline.

iv) Response (e.g. 75%) on all handicaps among patients with at least two handicaps at baseline, without worsening of more than 50% of these handicaps and without emergence of a new handicap with an increase of more than 50% from baseline.

Taken together with the results of the two phase 2 studies (examples 1 and 2), these exploratory data on a restricted mast cell mediator release associated handicap population (i.e. Hamilton rating for depression ≥14; Fatigue Impact Scale (FIS) score ≥75), along with new and stringent response criterion (example 3), provide evidence that therapeutic benefits of high clinical significance can be achieved in patients with indolent forms of mastocytosis (regardless of D816V c-Kit mutation status) when treated with a tyrosine kinase inhibitor or a mast cell inhibitor, and especially masitinib.

Example 4

A prospective, multicenter, randomized, double blind, placebo-controlled, 2-parallel group with a randomization 1:1, phase 3 study was performed to compare efficacy and safety of masitinib at 6 mg/kg/day to placebo in treatment of patients with documented smoldering systemic mastocytosis, indolent systemic mastocytosis or cutaneous mastocytosis, with (mild to moderate) handicap. The trial lasted 24 weeks with possible extension.

In accordance with protocol amendment version 7.0 (v7), the study population was amended to a more restricted subpopulation of mastocytosis. The objective therefore became to compare efficacy and safety of masitinib at 6 mg/kg/day to placebo in treatment of patients with systemic mastocytosis with severe handicap. The trial lasted 24 weeks with possible extension.

Eligible patients according to the protocol v7 diagnostic criteria thus relate to a disease for which the following criteria are fulfilled:
1. Patient with one of the following documented mastocytosis as per WHO classification:
   a. Smoldering Systemic Mastocytosis;
   b. Indolent Systemic Mastocytosis; and/or
2. Patient with documented mastocytosis and evaluable disease based upon histological criteria including typical infiltrates of mast cells in a multifocal or diffuse pattern in skin and/or bone marrow biopsy.

The former inclusion criterion was applied to include non-aggressive forms of systemic mastocytosis according to WHO classification, while the latter selected patients matching those from the masitinib phase 2 trials, for which this is a confirmatory study. To ensure consistency in the Investigator's application of diagnostic criteria it was necessary to develop a new definition of systemic mastocytosis respecting criteria 1 and 2 of the protocol. To be noted, criterion 2 allows several possibilities for the combination of organs (bone marrow, skin, digestive organs, etc.) and allows for a diagnosis of systemic mastocytosis for patients who have mastocytes in bone marrow without any abnormality.

The resultant diagnostic criteria were referred to as the 'AB Science Systemic Mastocytosis (ABSSM) criteria', as described hereinabove. Thus, a diagnosis of systemic mastocytosis is verified if any the following four criteria are fulfilled at baseline or before baseline:

Presence of mast cells in any bone marrow biopsy or aspirate associated with at least one sign of abnormality, wherein said abnormal signs are:
  More than 1% infiltration of mast cells in bone marrow.
  Aggregates of more than 15 mast cells in bone marrow that can be described by the following words: nodules, seats, clusters, foci, or granuloma.
  More than 25% atypical mast cells in a sample of bone marrow.
  Abnormal mast cells in the sample of bone marrow with microscopic testing that can be described by the following words: spindled, abnormal, atypical, fusiform, dystrophic, pathologic, dysmorphic.
  Abnormal immunohistochemistry signs: mast cells in bone marrow express CD2 and/or CD25 present.
  c-Kit point mutation at codon 816 (c-Kit 816) in bone marrow.
Detection of c-Kit 816 in bone marrow without evidence of mast cells in bone marrow and detection of c-Kit 816 in skin biopsy justifying clonality.
Presence of mast cells in bone marrow biopsy or aspirate without signs of mast cell abnormality.
Excess of mast cells detected in digestive organs in addition to excess of mast cells in the skin.

The phase 3 study was designed to evaluate masitinib efficacy and safety in severe systemic mastocytosis patients, with or without D816V mutation of c-Kit.

Severe systemic mastocytosis was defined as the presence of at least two of the six following mast cell mediator release associated handicaps: a pruritus score ≥9; a number of flushes per week ≥8; a Hamilton rating scale for depression (HAMD-17) score ≥19; a number of stools per day ≥4; a number of micturition per day ≥8; a fatigue score (asthenia) measured by Fatigue Impact Scale ≥75, wherein at least one handicap is selected among pruritus, flushes, depression and fatigue (asthenia).

To be noted, for the purpose of efficacy analysis a patient was classified as severe if they suffered from at least one of the main handicaps constituting the primary endpoint: Pruritus score ≥9; number of flushes per week ≥8; Hamilton rating scale for depression (HAMD-17) score ≥19; Fatigue Impact Scale total score (asthenia) ≥75. The criterion of "at least two of the following handicaps" including handicaps on stools and micturition, was relaxed to "at least one of the main handicaps" (i.e. pruritus, flushes, depression and fatigue).

Patients enrolled in the phase 3 study had between one and four of the following severe mastocytosis related symptoms at baseline:
Pruritus score ≥9
Number of flushes per week ≥8
Depression measured by the Hamilton rating scale (HAMD-17) score ≥19
Asthenia measured by the Fatigue Impact Scale total score ≥75

The study enrolled 135 patients with severe systemic mastocytosis.

Patients with systemic mastocytosis with severe handicap were randomized in two treatment groups including: Group 1: patients received masitinib 6 mg/kg/day, and Group 2: patients received placebo. The two treatment groups were defined such as to equally balance handicap/scores at baseline regarding pruritus, flushes, depression and fatigue, which might influence the study outcome. The randomization procedures included a minimization process aimed at reducing any difference in the distribution of the handicaps/scores at baseline and country in patients with documented smoldering or indolent systemic mastocytosis with severe handicap.

Patients with one of the following documented mastocytosis as per WHO classification were excluded from the study: cutaneous mastocytosis; not documented smoldering systemic mastocytosis or indolent systemic mastocytosis; systemic mastocytosis with an associated clonal hematologic non mast cell lineage disease (SM-AHNMD); mast cell leukemia (MCL); or aggressive systemic mastocytosis (ASM).

Analysis Datasets:
Intention-to-Treat (ITT) Dataset—
The ITT population was defined as all patients randomized presenting a documented systemic mastocytosis with severe handicap as defined above (and as documented also by protocol version 7.0). Patients were classified according to the treatment-arm to which they have been randomized, irrespective of the actual treatment received.

Modified Intent-to-Treat (mITT) Dataset—
The mITT population included all ITT patients with severe systemic mastocytosis who took at least one dose of study treatment (masitinib/placebo).

Per Protocol (PP) Dataset—
The PP data set consisted of all patients of the mITT data set without any major protocol deviation. This was the set of patients who participated in the study as intended. Patients terminating the study prematurely were included in the PP data set provided that there was no protocol deviation. Before locking the data base, the precise reasons for excluding patients from the PP data set were fully defined and documented by the Data Review Committee. Protocol deviations were defined as: inclusion and non-inclusion criteria were not met, intake of forbidden medication, non-respect of visit dates, missing value for main criterion without premature termination, non-respect of protocol design, any other deviations during the course of the study.

Safety Population—
The safety population consists of all patients presenting a documented systemic mastocytosis with severe handicap as defined by protocol version 7.0 who took at least one dose of study medication (masitinib or placebo).

Statistical Methods:
Efficacy: Handicaps are defined as:
Main handicaps: pruritus score ≥9, number of flushes per week ≥8, HAMD-17 score ≥19, Fatigue Impact Scale ≥75;
Other handicaps: micturition ≥8, stools ≥4.
Response on a handicap is defined as an improvement ≥75% from baseline for pruritus, flushes, Hamilton, and fatigue.

Primary Analysis:
The primary objective of the phase 3 study was to detect a statistically significant difference between masitinib (plus concomitant symptomatic treatments) and placebo (plus concomitant symptomatic treatments) in cumulative response on four severe symptoms, referred to also as handicaps.

Cumulative Response by Patient*Handicap—
For all the patients, the response at each study visit (5 visits from week 8 to week 24) will be calculated on each handicap present at baseline (among pruritus, flushes, Hamilton and FIS) as defined above. Thus, from 5 to 20 responses will be calculated per patient: 5 if the patient presents only 1 handicap at baseline corresponding to the 5 visits, and 20 if the patient presents with 4 handicaps at baseline corresponding to the 4 handicaps times 5 visits.

Primary analysis (referred to as "4H75% response") was based on the comparison between masitinib and placebo in the number of actual responses between week 8 and week 24 divided by the total number of possible responses over the same treatment period. At each patient evaluation between weeks 8 and 24, each of the above four severe symptoms was evaluated. An improvement ≥75% with respect to baseline in one symptom represented one positive treatment response.

For qualitative binary variables, such as a response (yes/no), main analysis was performed with the Missing Data equal to Failure (MDF) method, and sensitivity analysis will performed on Observed Cases (OC, no replacement of the missing data) The MDF method is defined as follows:
Replacement of missing value for patients withdrawn from the study:
Case 1: discontinuation for toxicity, lack of efficacy, or unknown reason. In this case, missing data was imputed as failure (missing=failure as primary analysis).
Case 2: discontinuation for a documented reason excluding toxicity or lack of efficacy. In this case, non-observed values can be considered as Missing At Random (MAR), and no imputation will be done (Observed Cases).
Replacement of missing value for patients present at the visit: If data was missing despite the patient being present at the visit, said missing data was not replaced.

Secondary Analysis:
Secondary analyses were based on the following endpoints:
Cumulative 75%-response rate for pruritus (1H75% response)
Cumulative 75% response rate on the handicaps of pruritus or flushes (2H75% response)
Cumulative 75% response rate on the handicaps of pruritus or flushes or depression (3H75% response)
Mean change in tryptase level relative to baseline at week 24, in patients with baseline level ≥20 m/L.

The symptoms of pruritus and flush are well-recognized to be associated with mast cell activation in mastocytosis. Depression is a symptom that has an important impact on quality of life of patients suffering from mastocytosis, and is therefore of high clinical relevance. Tryptase is a biological product released by mast cells and an established marker of mast cell burden and activity.

Cumulative Response on Pruritus Among Patients with the Handicap at Baseline:
Cumulative response is calculated for pruritus because pruritus is considered as the most objective and representative measure in mastocytosis benefiting from a validated measure. For the patients presenting the handicap at baseline (i.e. score ≥9), the response at each study visit (5 visits from week 8 to week 24) will be calculated as defined above. Thus, 5 responses will be calculated by the patient for each secondary variable listed. Replacement of missing data was performed via the Missing Data equal to Failure (MDF) method for patients based on the rules described hereinbefore.

Cumulative Response on Pruritus and/or Flushes Among Patients with these Handicaps at Baseline:

Cumulative response is calculated for pruritus and/or flushes handicaps because these are direct markers of mast cell activity and therefore the most relevant symptoms of mastocytosis. Handicap at baseline is defined as: pruritus score ≥9 and flushes per week ≥8. Response is defined as an improvement with respect to the baseline values ≥75%. For all patients, the response at each study visit (5 visits from Week-8 to Week-24) will be calculated on each handicap present at baseline (among pruritus and flushes), as defined above. Thus, from 5 to 10 responses will be calculated per patient: 5 responses if the patient presents only 1 handicap at baseline (corresponding to the 5 visits) and 10 responses if the patient presents both handicaps at baseline (corresponding to the 2 handicaps times the 5 visits). Replacement of missing data was performed via the Missing Data equal to Failure (MDF) method for patients based on the rules described hereinbefore.

Example 5

The therapeutic benefits of a treatment with a tyrosine kinase inhibitor or a mast cell inhibitor, especially masitinib mesilate, were assessed in a subpopulation of patients suffering specifically from severe systemic mastocytosis with the presence of at least one severe mast cell mediator release associated handicap. Proof of concept that masitinib can generate a clinically relevant therapeutic benefit in the subpopulation of severe systemic mastocytosis is supported via post-hoc analysis of data from two phase 2 clinical trials conducted in a relevant patient population. A first phase 2 study was conducted in patients with indolent forms of mastocytosis with handicap and not bearing activating point mutations in the phosphotransferase domain of c-Kit such as the main mutation Asp-816-Val. A second phase 2 study was conducted in patients with mastocytosis with handicap and bearing activating point mutations in the phosphotransferase domain of c-Kit such as the main mutation Asp-816-Val. Subpopulation of Severe Systemic Mastocytosis (at Least One Severe Mast Cell Mediator Release Associated Handicap at Baseline from Among Pruritus, Flush Frequency, Fatigue, or Depression)

In one scenario, among those systemic mastocytosis patients from these pooled studies, 28 patients met the criteria for severe handicap at baseline, as defined as having at least one handicap selected from pruritus, flushes, fatigue or depression (defined respectively as: pruritus score ≥9, flushes frequency per week ≥8, FIS ≥75, or Hamilton score ≥19) with a total of 53 severe baseline handicaps reported (note that a given patient may present with more than one handicap). Assessment of treatment response on a handicap was defined as a ≥75% improvement from baseline on at least one handicap among pruritus, flushes, fatigue or depression. Results for overall response rates as well as relative changes in individual handicaps and response rates are presented in Table 11.

Overall, at week 12, there was a response rate of 28.3%. A significant improvement was observed for the variables of flushes frequency (p<0.001), pruritus (p=0.002) and FIS score (p=0.004), with an improving trend in the Hamilton score (p=0.063). At week 24, there was an overall response rate of 23.5%. The slight decrease in response rate between week 12 to week 24 was in part due to patients deciding not to enter the studies extension phases. However, statistically significant improvement was maintained over this time for the variables of flushes frequency (p<0.001), pruritus score (p=0.002) and FIS score (p=0.004) with again an improving trend in the Hamilton score (p=0.063).

Considering cumulative response analysis, i.e. the sum of actual responses between weeks 8 and 24 (3 time point: W8, W12, and W24) divided by the total number of possible responses over the same treatment period, the response rate was 26.1% (see Table 12).

TABLE 11

Masitinib treatment effect in pooled mastocytosis studies cohort simulating a subpopulation of severe systemic mastocytosis (at least one severe mast cell mediator release associated handicap at baseline from among pruritus, flush frequency, fatigue, or depression) - Overall response and individual handicap change.

|  |  | Week 12 | Week 24 |
| --- | --- | --- | --- |
| Overall response ≥75%*† |  | 25.0% | 23.5% |
| Number of flushes ≥8 | Relative change** | −64.6% (30.8) | −75.3% (30.0) |
|  | p value | <0.001 | <0.001 |
| Pruritus score ≥9 | Relative change** | −37.6% (43.3) | −34.5% (42.9) |
|  | p value | 0.002 | 0.003 |
| FIS score ≥75 | Relative change** | −27.2% (21.7) | −27.6% (25.1) |
|  | p value | <0.001 | <0.001 |
| Hamilton score ≥19 | Relative change** | −40.5% (37.1) | −42.0% (36.1) |
|  | p value | 0.063 | 0.063 |

*Response rate missing data considered as failure.
†Response defined as a ≥75% improvement from baseline on at least one handicap among pruritus, flushes, fatigue or depression.
**Mean relative change (%) with respect to baseline (SD), Last Observation Carried Forward.

Pruritus and Flushes are the Variables of Greatest Predictive Power

An analysis of response rates associated with specific handicap variables, as opposed to overall response rates, has unexpectedly and surprisingly revealed that masitinib provides greatest therapeutic benefit in the severe mast cell mediator release associated handicaps of pruritus and flushes (Table 12). An equally unexpected and surprising finding was that masitinib provided only minor response rates in the severe mast cell mediator release associated handicaps of depression, fatigue, micturition frequency (pollakiuria), and stool frequency (diarrhea), making them vulnerable to masking due placebo-effect, which is expected to be high in this indication (i.e. any treatment-effect is indiscernible with respect to placebo treatment). This contrast in predictive power is maintained when pairing variables of [flushes or pruritus] when compared with [Hamilton or FIS], with cumulative response rates of approximately 40% versus 10%, respectively (see Table 12).

TABLE 12

Breakdown of individual handicap response rates. Masitinib treatment effect in pooled cohort simulating a subpopulation of severe systemic mastocytosis (severe mast cell mediator release associated handicap at baseline from among pruritus, flush frequency, fatigue, or depression) - Breakdown of individual handicap response rates.

|  | Cumulative response rate (≥75%) from W8 to W24 (%) |
| --- | --- |
| Overall Response* | 26.1 |
| Flushes only | 52.8 |
| Pruritus only | 28.6 |
| Hamilton only | 16.7 |
| FIS only | 8.0 |

TABLE 12-continued

Breakdown of individual handicap response rates. Masitinib treatment effect in pooled cohort simulating a subpopulation of severe systemic mastocytosis (severe mast cell mediator release associated handicap at baseline from among pruritus, flush frequency, fatigue, or depression) - Breakdown of individual handicap response rates.

|  | Cumulative response rate (≥75%) from W8 to W24 (%) |
|---|---|
| Micturition frequency (pollakiuria) only | 1.8 |
| Stool frequency (diarrhea) only | 18.4 |
| Flushes or Pruritus** | 38.8 |
| Hamilton or FIS** | 10.3 |

*Overall response rate defined as proportion of patients reporting a ≥75% improvement from baseline on at least one handicap among pruritus, flushes, fatigue or depression.
**2-handicap response rate defined as proportion of patients reporting a ≥75% improvement from baseline on at least one handicap from [flushes or pruritus], or on at least one handicap from [Hamilton or FIS]. Analysis based on missing data considered as failure (observed cases after W12).

Consequently, those patients identified as having systemic mastocytosis with severe mast cell mediator release associated handicap of pruritus and/or flushes represent a highly distinct subgroup from the overall population of patients with indolent forms of mastocytosis with handicap, for which masitinib can be expected to provide a clinically relevant therapeutic benefit. That is to say, systemic mastocytosis with severe mast cell mediator release associated handicap of pruritus and/or flushes is a highly predictive biomarker for masitinib treatment efficacy in severe systemic mastocytosis.

Subpopulation of Systemic Mastocytosis with Severe Handicap in Pruritus and Flush Frequency In an alternative scenario, among those systemic mastocytosis patients from these pooled studies, 4 patients met the criteria for severe handicap at baseline, as defined as having handicaps of both pruritus and flushes (defined respectively as: pruritus score ≥9, and flushes frequency per week ≥8) with a total of 8 severe baseline handicaps reported. Assessment of treatment response on a handicap was defined as a ≥75% improvement from baseline on at least one handicap among pruritus or flushes. Results for overall response rates as well as relative changes in individual handicaps and response rates are presented in Table 13. Overall, at week 24 there was a response rate of 50.0%. An improving trend was observed for pruritus and flush variables, this subgroup size probably being too small to demonstrate statistical significance.

TABLE 13

Masitinib treatment effect in pooled mastocytosis studies cohort simulating a subpopulation of severe systemic mastocytosis (severe mast cell mediator release associated handicap at baseline of pruritus and flushes) - Overall response and individual handicap change.

|  |  | Week 12 | Week 24 |
|---|---|---|---|
| Overall response ≥75%*† |  | 1/8 (12.5%) | 4/8 (50.0%) |
| Number of flushes ≥8 | Relative change** | −50.3 (27.8) | −82.9 (27.9) |
|  | p value | 0.125 | 0.125 |
| Pruritus score ≥9 | Relative change** | −12.9 (39.4) | −45.9 (63.9) |
|  | p value | 0.750 | 0.375 |

*Response rate missing data considered as failure.
†Response defined as a ≥75% improvement from baseline on at least one handicap among pruritus or flushes.
**Mean relative change (%) with respect to baseline (SD), Last Observation Carried Forward.

Example 6

Clinical data have shown that masitinib provides therapeutic benefit to a highly distinct subpopulation of mastocytosis patients, with the severity of mast cell mediator release associated handicaps serving as an independent predictor factor for treatment efficacy. These findings are without precedent because the predictive therapeutic significance of mast cell mediator release associated handicap severity in mastocytosis patients was previously unknown, in particular the predictive therapeutic significance of severe pruritus and severe flush handicaps.

A prospective, multicenter, randomized, placebo-controlled, parallel-group, phase 3 study, evaluated the efficacy and safety of masitinib (6 mg/kg/day administered orally in two daily intakes over 24-weeks with a double-blind extension phase possible) for the treatment of indolent systemic mastocytosis, smoldering systemic mastocytosis or cutaneous mastocytosis, in patients with mast cell mediator release symptoms that were refractory to conventional symptomatic treatment (see Example 4).

For analysis of masitinib's treatment-effect according to severity of mast cell mediator release associated handicaps a comparison was made between three patient groups derived from the overall study population.

One group comprised patients diagnosed as having indolent systemic mastocytosis or smoldering systemic mastocytosis with severe mast cell mediator release symptoms. Severe mastocytosis was defined as patients having at least two of the six following mast cell mediator release associated handicaps at baseline: pruritus score ≥9, number of flushes per week ≥8, Hamilton rating scale for depression (HAMD-17) score ≥19, a fatigue score (asthenia) measured by Fatigue Impact Scale (FIS) ≥75, number of stools per day ≥4 (diarrhea), number of micturition per day ≥8 (pollakiuria), wherein at least one handicap is selected among pruritus, flushes, depression and fatigue. (asthenia).

A second group comprised patients diagnosed as having severe indolent systemic mastocytosis, severe smoldering systemic mastocytosis, or severe cutaneous mastocytosis. Hence, this subpopulation is less restricted with inclusion of cutaneous mastocytosis having severe mast cell mediator release symptoms at baseline. This group provides comparative analysis for patient selection according to variant of mastocytosis (i.e. systemic versus cutaneous).

A third group comprised all randomized patients to study AB06006, corresponding therefore to the least restricted population, comprising patients with severe/non severe indolent and smoldering systemic mastocytosis, and severe/non severe cutaneous mastocytosis. This group provides comparative analysis based on patient selection according to severity of mast cell mediator release symptoms.

Results for various measures of treatment-effect, i.e. response rates and mean change relative to baseline, are presented in Tables 14 to 16 for the aforementioned patient groups. These data demonstrate that masitinib generates a clinical advantage in the subpopulation of severe systemic mastocytosis that is unexpectedly superior to other patient cohorts. The data presented in this example, and also in parts of the patent Description, are in part taken from preliminary analysis (cut-off date November 2015) and as such represent a close approximation to the final, validated dataset.

Tables 14 and 15 show that masitinib generates a clinical advantage in the subpopulation of severe indolent/smoldering systemic mastocytosis that is unexpectedly superior to other patient cohorts. This is evidenced by (i) statistically significant masitinib treatment-effect when compared with placebo (according to the 4H[75%], 3H[75%], 2H[75%] response criteria) that is not apparent in the comparator patient populations, and (ii) the relative improvement in treatment-effect response between populations (according to the variable Factor Diff).

Table 14 provides a comparison between the subpopulations of severe indolent/smoldering systemic mastocytosis versus severe cutaneous/indolent/smoldering mastocytosis with response criteria according to severe baseline handicaps.

Table 15 provides a comparison between the subpopulations of severe indolent/smoldering systemic mastocytosis versus all randomized patients with response criteria according to moderate baseline handicaps. In this case the number of baseline handicaps considered is greater because of the less stringent thresholds on baseline handicap definition. This analysis is necessary for matched comparison with the overall study population, i.e. for inclusion of non-severe patients.

Table 16 provides a comparison between the subpopulations of indolent/smoldering systemic mastocytosis with severe baseline handicap versus all randomized patients with respect to mean relative change in pruritus score from baseline at week 24. The symptom of pruritus is well-recognized to be associated with mast cell activation in mastocytosis and therefore provides a direct measure of treatment-effect on mast cell activity. From this it is evident that the masitinib treatment-effect is substantially greater (approximately 6-fold) for the severe indolent/smoldering systemic mastocytosis cohort when compared with the overall population.

Taken together, these data demonstrate that masitinib generates a clinical advantage in the restricted population of severe systemic mastocytosis that is unexpectedly superior to other patient cohorts. These findings support the use of severity of mast cell mediator release associated handicaps as an independent predictor factor for masitinib treatment efficacy and patient selection from among non-aggressive forms of mastocytosis.

Definitions

† Comparison of severe baseline handicaps in given population, wherein said severe handicap is defined as: pruritus score ≥9, number of flushes per week ≥8, Hamilton rating scale for depression (HAMD-17) score ≥19, Fatigue Impact Scale (FIS) total score ≥75.

‡ Comparison of moderate baseline handicaps in given population, wherein said moderate handicap is defined as: pruritus score ≥6, number of flushes per week ≥7; HAMD-17≥10, FIS ≥40.

NS=non significant

Diff=absolute difference in response rates between treatment-arms of a given population (masitinib arm minus placebo arm).

Factor Diff=ratio of 'Diff' between compared populations showing relative superiority of response rate for severe systemic population over the comparator population.

Cumulative response was defined as the sum of actual responses between weeks 8 and 24 (5 time points with visits scheduled every 4 weeks) divided by the total number of possible responses over the same treatment period. Response was defined as a decrease in baseline symptom by 75%.

*4H[75%] (primary efficacy analysis outcome measure)=cumulative response on at least one of four baseline handicaps selected from pruritus, flushes, depression, and asthenia in the mITT population with missing data considered as failure. Response was defined as a decrease in baseline symptom by 75%.

**3H[75%]=cumulative response on pruritus or flushes or depression in the mITT population with missing data considered as failure. Response was defined as a decrease in baseline symptom by 75%.

***2H[75%]=cumulative response on pruritus or flushes in the mITT population with missing data considered as failure. Response was defined as a decrease in baseline symptom by 75%.

****PF=patients with both pruritus and flushes handicap at baseline. Response was defined as a decrease in baseline symptom by 75%.

TABLE 14

Summary of response analyses according to severe baseline handicap, comparing patients with severe indolent/smoldering systemic mastocytosis against patients with severe cutaneous/indolent/smoldering mastocytosis.

| Severe baseline Cumulative Response, (%) | Severe indolent/smoldering systemic† | | | | Severe cutaneous/indolent/smoldering† | | | | |
|---|---|---|---|---|---|---|---|---|---|
| | Masitinib (n = 67) | Placebo (n = 62) | P | Diff (%) | Masitinib (n = 110) | Placebo (n = 110) | P | Diff (%) | Factor Diff |
| 4H[75%]* | 18.6 | 7.5 | 0.02 | 11.1 | 15.4 | 12.1 | NS | 3.3 | 3.4 |
| 3H[75%]** | 24.9 | 9.7 | 0.01 | 15.2 | 20.0 | 13.7 | NS | 6.3 | 2.4 |
| 2H[75%]*** | 27.2 | 10.7 | 0.04 | 16.5 | 22.0 | 14.6 | NS | 7.4 | 2.2 |
| PF**** | 35.4 | 17.6 | NS | 17.8 | 30.6 | 23.7 | NS | 6.9 | 2.6 |

TABLE 15

Summary of response analyses according to moderate baseline handicap comparing patients with severe indolent/smoldering systemic mastocytosis against all randomized patients to study AB06006 (comprising patients with severe/non severe indolent and smoldering systemic mastocytosis, and severe/non severe cutaneous mastocytosis).

| Moderate baseline Cumulative Response, (%) | Severe indolent/smoldering systemic‡ | | | | All patients (systemic/cutaneous, severe/non severe)‡ | | | | Factor Diff |
|---|---|---|---|---|---|---|---|---|---|
| | Masitinib (n = 67) | Placebo (n = 62) | P | Diff (%) | Masitinib (n = 110) | Placebo (n = 110) | P | Diff (%) | |
| 4H[75%]* | 19.6 | 9.5 | 0.03 | 10.1 | 16.3 | 15.9 | NS | 0.4 | 25.3 |
| 3H[75%]** | 24.8 | 12.0 | 0.02 | 12.8 | 20.3 | 18.0 | NS | 2.3 | 5.6 |
| 2H[75%]*** | 28.2 | 16.0 | 0.05 | 12.2 | 23.3 | 20.4 | NS | 2.9 | 4.2 |
| PF**** | 28.7 | 18.0 | NS | 10.7 | 26.9 | 26.7 | NS | 0.2 | 53.5 |

TABLE 16

Mean relative change in pruritus from baseline at week 24 comparing severe indolent/smoldering systemic mastocytosis patients with severe handicap at baseline against all randomized patients to study AB06006 (comprising patients with severe/non severe indolent and smoldering systemic mastocytosis, and severe/non severe cutaneous mastocytosis).

| Relative change (mean ± SD)† | Severe indolent/smoldering systemic† | | | All patients (systemic/cutaneous, severe/non severe)‡ | | | Factor Diff |
|---|---|---|---|---|---|---|---|
| | Masitinib (n = 67) | Placebo (n = 62) | Diff | Masitinib (n = 110) | Placebo (n = 110) | Diff | |
| Pruritus | −35.45 ± 41.33 | −22.49 ± 29.68 | 13.0 | −35.86 ± 43.12 | −33.55 ± 40.18 | 2.3 | 5.7 |

The invention claimed is:

1. A method for treating severe systemic mastocytosis in a human patient in need thereof comprising administering to said patient masitinib or a pharmaceutically acceptable salt or solvate thereof at a dose of 3.0, 4.5, 6.0, 7.5 or 9.0 mg per kg body weight per day (mg/kg/day),
wherein said patient is bearing a c-Kit D816V mutation, and
wherein said severe mastocytosis in said patient is associated with at least two mast cell mediator release associated handicaps selected from the group consisting of: a pruritus score ≥9; a number of flushes per week ≥8; a Hamilton rating scale for depression (HAMD-17) score ≥19; a number of stools per day ≥4; a number of micturition per day ≥8; and a fatigue score (asthenia) measured by Fatigue Impact Scale (FIS) ≥75, and
wherein at least one of the at least two selected handicaps is selected from the group consisting of a pruritus score ≥9, a number of flushes per week ≥8, a HAMD-17 score ≥19 and a fatigue score (asthenia) measured by FIS ≥75.

2. The method according to claim 1, wherein said severe systemic mastocytosis in said patient is associated with at least two mast cell mediator release associated handicaps selected from the group consisting of a pruritus score ≥9; a number of flushes per week ≥8; a HAMD-17 score ≥19; and a fatigue score measured by FIS ≥75.

3. The method according to claim 1, wherein at least one of the at least two selected mast cell mediator release associated handicaps is selected from the group consisting of a pruritus score ≥9 and a number of flushes per week ≥8.

4. The method according to claim 1, wherein the at least two selected mast cell mediator release associated handicaps are selected from the group consisting of a pruritus score ≥9; a number of flushes per week ≥8; and a HAMD-17 score ≥19.

5. The method according to claim 1, wherein said severe systemic mastocytosis in said patient is associated with the three mast cell mediator release associated handicaps: a pruritus score ≥9; a number of flushes per week ≥8; and a HAMD-17 score ≥19.

6. The method according to claim 1, wherein said severe systemic mastocytosis in said patient is further associated with asthenia with a fatigue score measured by FIS ≥75 or any equivalent cut-off determined using the FSS (Fatigue Severity Scale), FSI (Fatigue Symptom Inventory), BFI (Brief Fatigue Inventory) or MAF (Multidimensional Assessment of Fatigue).

7. The method according to claim 1, wherein said severe systemic mastocytosis in said patient is associated with a pruritus score ≥9 and a number of flushes per week ≥8.

8. The method according to claim 1, wherein said severe systemic mastocytosis is defined by the World Health Organization (WHO) diagnostic criteria.

9. The method according to claim 1, wherein said severe systemic mastocytosis relates to a disease which, at baseline or before baseline, meets a criterion selected from the group consisting of:
presence of mast cells in any bone marrow biopsy or aspirate associated with at least one sign of abnormality, wherein said abnormal signs are selected from the list comprising: more than 1% infiltration of mast cells in bone marrow; aggregates of more than 15 mast cells in bone marrow that can be described by the following words: nodules, seats, clusters, foci, or granuloma; more than 25% atypical mast cells in a sample of bone marrow; abnormal mast cells in the sample of bone marrow with microscopic testing that can be described by the following words: spindled, abnormal, atypical, fusiform, dystrophic, pathologic, dysmorphic; abnormal immunohistochemistry signs: mast cells in bone marrow express CD2 and/or CD25 present; and c-Kit point mutation at codon 816 (c-Kit 816) in bone marrow;

detection of c-Kit 816 in bone marrow without evidence of mast cells in bone marrow and detection of c-Kit 816 in skin biopsy justifying clonality;

presence of mast cells in bone marrow biopsy or aspirate without signs of mast cell abnormality; and excess of mast cells detected in digestive organs in addition to excess of mast cells in the skin.

10. The method according to claim 1, wherein said severe systemic mastocytosis relates to a disease for which the following criteria are fulfilled:

patient with one of the following documented mastocytosis as per WHO classification: smoldering systemic mastocytosis or indolent systemic mastocytosis; and/or patient with documented mastocytosis and evaluable disease based upon histological criteria including typical infiltrates of mast cells in a multifocal or diffuse pattern in skin and/or bone marrow biopsy.

11. The method according to claim 1, wherein said severe systemic mastocytosis is smoldering systemic mastocytosis or indolent systemic mastocytosis.

12. The method according to claim 1, wherein said pharmaceutically acceptable salt or solvate of masitinib is masitinib mesilate.

13. The method according to claim 1, wherein said masitinib, or a pharmaceutically acceptable salt or solvate thereof, is initially administered at a dose of 3.0 mg/kg/day during at least 4 weeks, then 4.5 mg/kg/day during at least 4 weeks, and at 6 mg/kg/day thereafter, with each dose escalation being subjected to toxicity controls.

14. The method according to claim 1, wherein said masitinib, or a pharmaceutically acceptable salt or solvate thereof, is administered in two daily intakes.

15. The method according to claim 1, wherein said masitinib, or a pharmaceutically acceptable salt or solvate thereof, is administered orally.

16. The method according to claim 1, wherein said masitinib, or a pharmaceutically acceptable salt or solvate thereof, is comprised in a pharmaceutical composition in an amount of at least 50 mg and less than 600 mg.

17. The method according to claim 1, wherein said masitinib, or a pharmaceutically acceptable salt or solvate thereof, is comprised in a pharmaceutical composition in an amount of at least 100 mg and less than 400 mg.

18. The method according to claim 1, wherein said severe systemic mastocytosis is indolent systemic mastocytosis.

* * * * *